US008349589B2

(12) United States Patent
De Boer et al.

(10) Patent No.: US 8,349,589 B2
(45) Date of Patent: *Jan. 8, 2013

(54) NON-NATURAL RECOMBINANT GELATINS WITH ENHANCED FUNCTIONALITY

(75) Inventors: Arjo Lysander De Boer, Tilburg (NL); Hendrik Van Urk, Tilburg (NL); Jan Bastiaan Bouwstra, Tilburg (NL); Peter Franciscus Theresius Maria Van Asten, Tilburg (NL)

(73) Assignee: Fujifilm Manufacturing Europe B.V., Tilburg (NL)

( * ) Notice: Subject to any disclaimer, the term of this patent is extended or adjusted under 35 U.S.C. 154(b) by 514 days.

This patent is subject to a terminal disclaimer.

(21) Appl. No.: 12/528,044

(22) PCT Filed: Feb. 21, 2008

(86) PCT No.: PCT/NL2008/050104
§ 371 (c)(1),
(2), (4) Date: Aug. 20, 2009

(87) PCT Pub. No.: WO2008/103044
PCT Pub. Date: Aug. 28, 2008

(65) Prior Publication Data
US 2010/0105618 A1 Apr. 29, 2010

(30) Foreign Application Priority Data

Feb. 12, 2007 (EP) .................................. 07102839
Feb. 21, 2007 (EP) .................................. 07102838
Sep. 12, 2007 (EP) .................................. 07116189
Sep. 12, 2007 (EP) .................................. 07116193
Jan. 16, 2008 (EP) .................................. 08100556

(51) Int. Cl.
*C12P 21/06* (2006.01)
*C07K 14/00* (2006.01)

(52) U.S. Cl. ........................... 435/69.1; 530/350; 514/1
(58) Field of Classification Search ................ 435/69.1; 530/350; 514/1
See application file for complete search history.

(56) References Cited

U.S. PATENT DOCUMENTS

| 4,855,134 | A | 8/1989 | Yamahira et al. ............ 424/85.7 |
| 5,002,769 | A | 3/1991 | Friedman ...................... 424/422 |
| 5,023,082 | A | 6/1991 | Friedman et al. ............. 424/426 |
| 5,399,361 | A | 3/1995 | Song et al. ................... 424/486 |
| 5,512,301 | A | 4/1996 | Song et al. ................... 424/484 |
| 5,597,578 | A | 1/1997 | Brown et al. ................. 424/422 |
| 5,733,994 | A | 3/1998 | Koepff et al. ................. 527/207 |
| 5,897,879 | A | 4/1999 | Friedman et al. ............. 424/486 |
| 6,068,854 | A | 5/2000 | Wunderlich et al. .......... 424/464 |
| 6,140,072 | A | 10/2000 | Ferrari et al. ................. 435/69.1 |
| 6,150,081 | A | 11/2000 | Van Heerde et al. ......... 430/569 |
| 6,342,250 | B1 | 1/2002 | Masters ........................ 424/484 |
| 6,458,386 | B1 | 10/2002 | Schacht et al. ................ 424/488 |
| 6,831,058 | B1 | 12/2004 | Ikada et al. ......................... 514/2 |
| 6,992,172 | B1 | 1/2006 | Chang et al. ................... 530/354 |
| 7,517,954 | B2 | 4/2009 | Bouwstra et al. ............. 530/350 |
| 7,598,347 | B2 * | 10/2009 | Bouwstra et al. ............. 530/350 |
| 2002/0028243 | A1 | 3/2002 | Masters ......................... 424/484 |
| 2002/0106410 | A1 | 8/2002 | Masters ......................... 424/484 |
| 2003/0007991 | A1 | 1/2003 | Masters ......................... 424/423 |
| 2003/0064074 | A1 | 4/2003 | Chang et al. ................. 424/184.1 |
| 2004/0237663 | A1 | 12/2004 | Farber et al. ................. 73/861.08 |
| 2005/0058703 | A1 | 3/2005 | Chang et al. ................... 424/456 |
| 2005/0119170 | A1 | 6/2005 | Bouwstra et al. ............... 514/12 |
| 2005/0147690 | A1 | 7/2005 | Masters et al. ................ 424/499 |
| 2005/0208141 | A1 | 9/2005 | Farber et al. .................. 424/488 |
| 2005/0229264 | A1 | 10/2005 | Chang et al. ..................... 800/8 |
| 2005/0238663 | A1 | 10/2005 | Hunt ........................... 424/239.1 |
| 2006/0024346 | A1 | 2/2006 | Brody et al. .................. 424/423 |
| 2006/0024361 | A1 | 2/2006 | Odidi et al. ................... 424/464 |
| 2006/0068013 | A1 | 3/2006 | DiTizio et al. ................ 424/484 |
| 2006/0121609 | A1 | 6/2006 | Yannas et al. ................. 435/395 |
| 2006/0147501 | A1 | 7/2006 | Hillas et al. .................. 424/443 |
| 2006/0177492 | A1 | 8/2006 | Yunoki et al. ................. 424/445 |
| 2006/0204551 | A1 | 9/2006 | Bouwstra et al. ........... 424/185.1 |
| 2006/0241032 | A1 | 10/2006 | Bouwstra et al. ............... 514/12 |
| 2006/0251719 | A1 | 11/2006 | Tabata ........................... 424/468 |
| 2007/0004034 | A1 | 1/2007 | Bouwstra et al. ........... 435/289.1 |
| 2007/0009580 | A1 | 1/2007 | DiCosmo et al. ............. 424/443 |
| 2007/0031501 | A1 | 2/2007 | Van Es et al. ................. 424/489 |
| 2007/0190153 | A1 | 8/2007 | Farber .......................... 424/488 |
| 2007/0196496 | A1 | 8/2007 | Farber et al. .................. 424/488 |
| 2008/0107666 | A1 | 5/2008 | van Es et al. ............... 424/185.1 |
| 2008/0113910 | A1 | 5/2008 | Bouwstra et al. ............... 514/12 |
| 2008/0114078 | A1 | 5/2008 | Bouwstra et al. .............. 514/774 |
| 2008/0167446 | A1 | 7/2008 | Bouwstra et al. ............. 530/354 |
| 2008/0274957 | A1 | 11/2008 | Bouwstra et al. ............... 514/12 |
| 2009/0143568 | A1 | 6/2009 | Chang et al. ................... 530/354 |

FOREIGN PATENT DOCUMENTS

| JP | 2005-211477 | 8/2005 |
| WO | WO 2004/056976 | 7/2004 |
| WO | WO 2004/085473 | 10/2004 |
| WO | WO 2005/011739 | 2/2005 |
| WO | WO 2007/073190 | 6/2007 |

OTHER PUBLICATIONS

Werten et al., "High-yield Secretion of Recombinant Gelatins by *Pichia pastoris*", Yeast, 15:1087-1096 (1999).
Báez at al., "Recombinant microbial systems for the production of human collagen and gelatin", Appl. Microbiol Biotechnol., 69:245-252 (2005).
Werten et al., "Secreted production of a custom-designed, highly hydrophilic gelatin in *Pichia pastoris*", Protein Engineering, 14(6):447-454 (2001).
Olsen at al., "Recombinant collagen and gelatin for drug delivery", Advanced Drug Delivery Reviews, Amsterdam, NL, 55(12):1547-1567 (2003).
Sutter et al., "Recombinant gelatin hydrogels for the sustained release of proteins", Journal of Controlled Release, 119:301-312 (2007).
Extracts from gmap-gelatin.com, dated Aug. 25, 2006.

* cited by examiner

*Primary Examiner* — Karen Cochrane Carlson
(74) *Attorney, Agent, or Firm* — Morgan, Lewis & Bockius LLP

(57) ABSTRACT

The invention concerns recombinant gelatin monomers and recombinant gelatins comprising or consisting of multimers of the monomers. The recombinant gelatins can be produced with enhanced stability.

12 Claims, No Drawings

SEQUENCE LISTING

<160> NUMBER OF SEQ ID NOS: 6

<210> SEQ ID NO 1
<211> LENGTH: 315
<212> TYPE: PRT
<213> ORGANISM: Artificial
<220> FEATURE:
<223> OTHER INFORMATION: PCM-monomer

<400> SEQUENCE: 1

```
Gly Glu Pro Gly Asn Pro Gly Ser Pro Gly Asn Gln Gly Gln Pro Gly
1               5                   10                  15

Asn Arg Gly Asp Lys Gly Ser Pro Gly Asn Pro Gly Gln Pro Gly Asn
            20                  25                  30

Glu Gly Gln Pro Gly Gln Pro Gly Gln Asn Gly Gln Pro Gly Glu Pro
```

```
                35                  40                  45
Gly Ser Asn Gly Pro Gln Gly Ser Gln Gly Asn Pro Gly Lys Asn Gly
         50                  55                  60

Gln Pro Gly Ser Pro Gly Ser Arg Gly Asp Gln Gly Ser Pro Gly Asn
 65                  70                  75                  80

Gln Gly Ser Pro Gly Gln Pro Gly Asn Pro Gly Gln Pro Gly Glu Gln
                 85                  90                  95

Gly Lys Pro Gly Asn Gln Gly Pro Ala Gly Glu Pro Gly Asn Pro Gly
            100                 105                 110

Ser Pro Gly Asn Gln Gly Gln Pro Gly Asn Lys Gly Ser Pro Gly Asn
        115                 120                 125

Pro Gly Gln Pro Gly Asn Arg Gly Asp Glu Gly Gln Pro Gly Gln Pro
    130                 135                 140

Gly Gln Asn Gly Gln Pro Gly Glu Pro Gly Ser Asn Gly Pro Gln Gly
145                 150                 155                 160

Ser Gln Gly Asn Pro Gly Lys Asn Gly Gln Pro Gly Ser Pro Gly Ser
                165                 170                 175

Gln Gly Ser Pro Gly Asn Gln Gly Ser Pro Gly Gln Pro Gly Asn Pro
            180                 185                 190

Gly Gln Pro Gly Glu Arg Gly Asp Gln Gly Lys Pro Gly Asn Gln Gly
        195                 200                 205

Pro Ala Gly Glu Pro Gly Asn Pro Gly Ser Pro Gly Asn Gln Gly Gln
    210                 215                 220

Pro Gly Asn Lys Gly Ser Pro Gly Asn Pro Gly Gln Pro Gly Asn Glu
225                 230                 235                 240

Gly Gln Pro Gly Gln Pro Gly Gln Arg Gly Asp Asn Gly Gln Pro Gly
                245                 250                 255

Glu Pro Gly Ser Asn Gly Pro Gln Gly Ser Gln Gly Asn Pro Gly Lys
            260                 265                 270

Asn Gly Gln Pro Gly Ser Pro Gly Ser Gln Gly Ser Pro Gly Asn Gln
        275                 280                 285

Gly Ser Pro Gly Gln Pro Gly Asn Pro Gly Gln Pro Gly Glu Gln Gly
    290                 295                 300

Lys Pro Gly Asn Arg Gly Asp Gln Gly Pro Ala
305                 310                 315

<210> SEQ ID NO 2
<211> LENGTH: 320
<212> TYPE: PRT
<213> ORGANISM: Artificial
<220> FEATURE:
<223> OTHER INFORMATION: PCM

<400> SEQUENCE: 2

Gly Pro Pro Gly Glu Pro Gly Asn Pro Gly Ser Pro Gly Asn Gln Gly
1               5                  10                  15

Gln Pro Gly Asn Arg Gly Asp Lys Gly Ser Pro Gly Asn Pro Gly Gln
            20                  25                  30

Pro Gly Asn Glu Gly Gln Pro Gly Gln Pro Gly Gln Asn Gly Gln Pro
        35                  40                  45

Gly Glu Pro Gly Ser Asn Gly Pro Gln Gly Ser Gln Gly Asn Pro Gly
    50                  55                  60

Lys Asn Gly Gln Pro Gly Ser Pro Gly Ser Arg Gly Asp Gln Gly Ser
65                  70                  75                  80

Pro Gly Asn Gln Gly Ser Pro Gly Gln Pro Gly Asn Pro Gly Gln Pro
                85                  90                  95
```

```
Gly Glu Gln Gly Lys Pro Gly Asn Gln Gly Pro Ala Gly Glu Pro Gly
                100                 105                 110

Asn Pro Gly Ser Pro Gly Asn Gln Gly Gln Pro Gly Asn Lys Gly Ser
            115                 120                 125

Pro Gly Asn Pro Gly Gln Pro Gly Asn Arg Gly Asp Glu Gly Gln Pro
        130                 135                 140

Gly Gln Pro Gly Gln Asn Gly Gln Pro Gly Glu Pro Gly Ser Asn Gly
145                 150                 155                 160

Pro Gln Gly Ser Gln Gly Asn Pro Gly Lys Asn Gly Gln Pro Gly Ser
                165                 170                 175

Pro Gly Ser Gln Gly Ser Pro Gly Asn Gln Gly Ser Pro Gly Gln Pro
            180                 185                 190

Gly Asn Pro Gly Gln Pro Gly Glu Arg Gly Asp Gln Gly Lys Pro Gly
        195                 200                 205

Asn Gln Gly Pro Ala Gly Glu Pro Gly Asn Pro Gly Ser Pro Gly Asn
        210                 215                 220

Gln Gly Gln Pro Gly Asn Lys Gly Ser Pro Gly Asn Pro Gly Gln Pro
225                 230                 235                 240

Gly Asn Glu Gly Gln Pro Gly Gln Pro Gly Gln Arg Gly Asp Asn Gly
                245                 250                 255

Gln Pro Gly Glu Pro Gly Ser Asn Gly Pro Gly Gln Gly Ser Gln Gly Asn
            260                 265                 270

Pro Gly Lys Asn Gly Gln Pro Gly Ser Pro Gly Ser Gln Gly Ser Pro
        275                 280                 285

Gly Asn Gln Gly Ser Pro Gly Gln Pro Gly Asn Pro Gly Gln Pro Gly
        290                 295                 300

Glu Gln Gly Lys Pro Gly Asn Arg Gly Asp Gln Gly Pro Ala Gly Gly
305                 310                 315                 320

<210> SEQ ID NO 3
<211> LENGTH: 630
<212> TYPE: PRT
<213> ORGANISM: Artificial
<220> FEATURE:
<223> OTHER INFORMATION: PCM-dimer

<400> SEQUENCE: 3

Gly Glu Pro Gly Asn Pro Gly Ser Pro Gly Asn Gln Gly Gln Pro Gly
1               5                   10                  15

Asn Arg Gly Asp Lys Gly Ser Pro Gly Asn Pro Gly Gln Pro Gly Asn
            20                  25                  30

Glu Gly Gln Pro Gly Gln Pro Gly Gln Asn Gly Gln Pro Gly Glu Pro
        35                  40                  45

Gly Ser Asn Gly Pro Gln Gly Ser Gln Gly Asn Pro Gly Lys Asn Gly
50                  55                  60

Gln Pro Gly Ser Pro Gly Ser Arg Gly Asp Gln Gly Ser Pro Gly Asn
65                  70                  75                  80

Gln Gly Ser Pro Gly Gln Pro Gly Asn Pro Gly Gln Pro Gly Glu Gln
                85                  90                  95

Gly Lys Pro Gly Asn Gln Gly Pro Ala Gly Glu Pro Gly Asn Pro Gly
            100                 105                 110

Ser Pro Gly Asn Gln Gly Gln Pro Gly Asn Lys Gly Ser Pro Gly Asn
        115                 120                 125

Pro Gly Gln Pro Gly Asn Arg Gly Asp Glu Gly Gln Pro Gly Gln Pro
        130                 135                 140
```

```
Gly Gln Asn Gly Gln Pro Gly Glu Pro Gly Ser Asn Gly Pro Gln Gly
145                 150                 155                 160

Ser Gln Gly Asn Pro Gly Lys Asn Gly Gln Pro Gly Ser Pro Gly Ser
            165                 170                 175

Gln Gly Ser Pro Gly Asn Gln Gly Ser Pro Gly Gln Pro Gly Asn Pro
        180                 185                 190

Gly Gln Pro Gly Glu Arg Gly Asp Gln Gly Lys Pro Gly Asn Gln Gly
        195                 200                 205

Pro Ala Gly Glu Pro Gly Asn Pro Gly Ser Pro Gly Asn Gln Gly Gln
210                 215                 220

Pro Gly Asn Lys Gly Ser Pro Gly Asn Pro Gly Gln Pro Gly Asn Glu
225                 230                 235                 240

Gly Gln Pro Gly Gln Pro Gly Gln Arg Gly Asp Asn Gly Gln Pro Gly
            245                 250                 255

Glu Pro Gly Ser Asn Gly Pro Gln Gly Ser Gln Gly Asn Pro Gly Lys
            260                 265                 270

Asn Gly Gln Pro Gly Ser Pro Gly Ser Gln Gly Ser Pro Gly Asn Gln
        275                 280                 285

Gly Ser Pro Gly Gln Pro Gly Asn Pro Gly Gln Pro Gly Glu Gln Gly
        290                 295                 300

Lys Pro Gly Asn Arg Gly Asp Gln Gly Pro Ala Gly Glu Pro Gly Asn
305                 310                 315                 320

Pro Gly Ser Pro Gly Asn Gly Gln Pro Gly Asn Arg Gly Asp Lys
            325                 330                 335

Gly Ser Pro Gly Asn Pro Gly Gln Pro Gly Asn Glu Gln Pro Gly
        340                 345                 350

Gln Pro Gly Gln Asn Gly Gln Pro Gly Glu Pro Gly Ser Asn Gly Pro
        355                 360                 365

Gln Gly Ser Gln Gly Asn Pro Gly Lys Asn Gly Gln Pro Gly Ser Pro
        370                 375                 380

Gly Ser Arg Gly Asp Gln Gly Ser Pro Gly Asn Gln Gly Ser Pro Gly
385                 390                 395                 400

Gln Pro Gly Asn Pro Gly Gln Pro Gly Glu Gln Gly Lys Pro Gly Asn
            405                 410                 415

Gln Gly Pro Ala Gly Glu Pro Gly Asn Pro Gly Ser Pro Gly Asn Gln
        420                 425                 430

Gly Gln Pro Gly Asn Lys Gly Ser Pro Gly Asn Pro Gly Gln Pro Gly
        435                 440                 445

Asn Arg Gly Asp Glu Gly Gln Pro Gly Gln Pro Gly Gln Asn Gly Gln
450                 455                 460

Pro Gly Glu Pro Gly Ser Asn Gly Pro Gln Gly Ser Gln Gly Asn Pro
465                 470                 475                 480

Gly Lys Asn Gly Gln Pro Gly Ser Pro Gly Ser Gln Gly Ser Pro Gly
            485                 490                 495

Asn Gln Gly Ser Pro Gly Gln Pro Gly Asn Pro Gly Gln Pro Gly Glu
        500                 505                 510

Arg Gly Asp Gln Gly Lys Pro Gly Asn Gln Gly Pro Ala Gly Glu Pro
        515                 520                 525

Gly Asn Pro Gly Ser Pro Gly Asn Gln Gly Pro Gly Asn Lys Gly
        530                 535                 540

Ser Pro Gly Asn Pro Gly Gln Pro Gly Asn Glu Gly Gln Pro Gly Gln
545                 550                 555                 560

Pro Gly Gln Arg Gly Asp Asn Gly Gln Pro Gly Glu Pro Gly Ser Asn
            565                 570                 575
```

```
Gly Pro Gln Gly Ser Gln Gly Asn Pro Gly Lys Asn Gly Gln Pro Gly
            580                 585                 590
Ser Pro Gly Ser Gln Gly Ser Pro Gly Asn Gln Gly Ser Pro Gly Gln
        595                 600                 605
Pro Gly Asn Pro Gly Gln Pro Gly Glu Gln Gly Lys Pro Gly Asn Arg
    610                 615                 620
Gly Asp Gln Gly Pro Ala
625                 630

<210> SEQ ID NO 4
<211> LENGTH: 635
<212> TYPE: PRT
<213> ORGANISM: Artificial
<220> FEATURE:
<223> OTHER INFORMATION: PCM2

<400> SEQUENCE: 4

Gly Pro Pro Gly Glu Pro Gly Asn Pro Gly Ser Pro Gly Asn Gln Gly
1               5                   10                  15
Gln Pro Gly Asn Arg Gly Asp Lys Gly Ser Pro Gly Asn Pro Gly Gln
            20                  25                  30
Pro Gly Asn Glu Gly Gln Pro Gly Gln Pro Gly Gln Asn Gly Gln Pro
        35                  40                  45
Gly Glu Pro Gly Ser Asn Gly Pro Gln Gly Ser Gln Gly Asn Pro Gly
    50                  55                  60
Lys Asn Gly Gln Pro Gly Ser Pro Gly Ser Arg Gly Asp Gln Gly Ser
65                  70                  75                  80
Pro Gly Asn Gln Gly Ser Pro Gly Gln Pro Gly Asn Pro Gly Gln Pro
            85                  90                  95
Gly Glu Gln Gly Lys Pro Gly Asn Gln Gly Pro Ala Gly Glu Pro Gly
        100                 105                 110
Asn Pro Gly Ser Pro Gly Asn Gln Gly Gln Pro Gly Asn Lys Gly Ser
    115                 120                 125
Pro Gly Asn Pro Gly Gln Pro Gly Asn Arg Gly Asp Glu Gly Gln Pro
130                 135                 140
Gly Gln Pro Gly Gln Asn Gly Gln Pro Gly Glu Pro Gly Ser Asn Gly
145                 150                 155                 160
Pro Gln Gly Ser Gln Gly Asn Pro Gly Lys Asn Gly Gln Pro Gly Ser
            165                 170                 175
Pro Gly Ser Gln Gly Ser Pro Gly Asn Gln Gly Ser Pro Gly Gln Pro
        180                 185                 190
Gly Asn Pro Gly Gln Pro Gly Glu Arg Gly Asp Gln Gly Lys Pro Gly
    195                 200                 205
Asn Gln Gly Pro Ala Gly Glu Pro Gly Asn Pro Gly Ser Pro Gly Asn
210                 215                 220
Gln Gly Gln Pro Gly Asn Lys Gly Ser Pro Gly Asn Pro Gly Gln Pro
225                 230                 235                 240
Gly Asn Glu Gly Gln Pro Gly Gln Pro Gly Gln Arg Gly Asp Asn Gly
            245                 250                 255
Gln Pro Gly Glu Pro Gly Ser Asn Gly Pro Gln Gly Ser Gln Gly Asn
        260                 265                 270
Pro Gly Lys Asn Gly Gln Pro Gly Ser Pro Gly Ser Gln Gly Ser Pro
    275                 280                 285
Gly Asn Gln Gly Ser Pro Gly Gln Pro Gly Asn Pro Gly Gln Pro Gly
290                 295                 300
```

-continued

```
Glu Gln Gly Lys Pro Gly Asn Arg Gly Asp Gln Gly Pro Ala Gly Glu
305                 310                 315                 320

Pro Gly Asn Pro Gly Ser Pro Gly Asn Gln Gly Pro Gly Asn Arg
            325                 330                 335

Gly Asp Lys Gly Ser Pro Gly Asn Pro Gly Gln Pro Gly Asn Glu Gly
        340                 345                 350

Gln Pro Gly Gln Pro Gly Gln Asn Gly Gln Pro Gly Glu Pro Gly Ser
        355                 360                 365

Asn Gly Pro Gln Gly Ser Gln Gly Asn Pro Gly Lys Asn Gly Gln Pro
370                 375                 380

Gly Ser Pro Gly Ser Arg Gly Asp Gln Gly Ser Pro Gly Asn Gln Gly
385                 390                 395                 400

Ser Pro Gly Gln Pro Gly Asn Pro Gly Gln Pro Gly Glu Gln Gly Lys
            405                 410                 415

Pro Gly Asn Gln Gly Pro Ala Gly Glu Pro Gly Asn Pro Gly Ser Pro
            420                 425                 430

Gly Asn Gln Gly Gln Pro Gly Asn Lys Gly Ser Pro Gly Asn Pro Gly
            435                 440                 445

Gln Pro Gly Asn Arg Gly Asp Glu Gly Gln Pro Gly Gln Pro Gly Gln
        450                 455                 460

Asn Gly Gln Pro Gly Glu Pro Gly Ser Asn Gly Pro Gln Gly Ser Gln
465                 470                 475                 480

Gly Asn Pro Gly Lys Asn Gly Gln Pro Gly Ser Pro Gly Ser Gln Gly
            485                 490                 495

Ser Pro Gly Asn Gln Gly Ser Pro Gly Gln Pro Gly Asn Pro Gly Gln
        500                 505                 510

Pro Gly Glu Arg Gly Asp Gln Gly Lys Pro Gly Asn Gln Gly Pro Ala
        515                 520                 525

Gly Glu Pro Gly Asn Pro Gly Ser Pro Gly Asn Gln Gly Gln Pro Gly
    530                 535                 540

Asn Lys Gly Ser Pro Gly Asn Pro Gly Gln Pro Gly Asn Glu Gly Gln
545                 550                 555                 560

Pro Gly Gln Pro Gly Gln Arg Gly Asp Asn Gly Gln Pro Gly Glu Pro
            565                 570                 575

Gly Ser Asn Gly Pro Gln Gly Ser Gln Gly Asn Pro Gly Lys Asn Gly
        580                 585                 590

Gln Pro Gly Ser Pro Gly Ser Gln Gly Ser Pro Gly Asn Gln Gly Ser
        595                 600                 605

Pro Gly Gln Pro Gly Asn Pro Gly Gln Pro Gly Glu Gln Gly Lys Pro
    610                 615                 620

Gly Asn Arg Gly Asp Gln Gly Pro Ala Gly Gly
625                 630                 635

<210> SEQ ID NO 5
<211> LENGTH: 1260
<212> TYPE: PRT
<213> ORGANISM: Artificial
<220> FEATURE:
<223> OTHER INFORMATION: PCM-tetramer

<400> SEQUENCE: 5

Gly Glu Pro Gly Asn Pro Gly Ser Pro Gly Asn Gln Gly Gln Pro Gly
1               5                   10                  15

Asn Arg Gly Asp Lys Gly Ser Pro Gly Asn Pro Gly Gln Pro Gly Asn
            20                  25                  30

Glu Gly Gln Pro Gly Gln Pro Gly Gln Asn Gly Gln Pro Gly Glu Pro
```

-continued

```
            35                  40                  45
Gly Ser Asn Gly Pro Gln Gly Ser Gln Gly Asn Pro Gly Lys Asn Gly
            50                  55                  60
Gln Pro Gly Ser Pro Gly Ser Arg Gly Asp Gln Gly Ser Pro Gly Asn
 65                  70                  75                  80
Gln Gly Ser Pro Gly Gln Pro Gly Asn Pro Gly Gln Pro Gly Glu Gln
                    85                  90                  95
Gly Lys Pro Gly Asn Gln Gly Pro Ala Gly Glu Pro Gly Asn Pro Gly
                   100                 105                 110
Ser Pro Gly Asn Gln Gly Gln Pro Gly Asn Lys Gly Ser Pro Gly Asn
                   115                 120                 125
Pro Gly Gln Pro Gly Asn Arg Gly Asp Glu Gly Gln Pro Gly Gln Pro
                   130                 135                 140
Gly Gln Asn Gly Gln Pro Gly Glu Pro Gly Ser Asn Gly Pro Gln Gly
145                 150                 155                 160
Ser Gln Gly Asn Pro Gly Lys Asn Gly Gln Pro Gly Ser Pro Gly Ser
                   165                 170                 175
Gln Gly Ser Pro Gly Asn Gln Gly Ser Pro Gly Gln Pro Gly Asn Pro
                   180                 185                 190
Gly Gln Pro Gly Glu Arg Gly Asp Gln Gly Lys Pro Gly Asn Gln Gly
                   195                 200                 205
Pro Ala Gly Glu Pro Gly Asn Pro Gly Ser Pro Gly Asn Gln Gly Gln
210                 215                 220
Pro Gly Asn Lys Gly Ser Pro Gly Asn Pro Gly Gln Pro Gly Asn Glu
225                 230                 235                 240
Gly Gln Pro Gly Gln Pro Gly Gln Arg Gly Asp Asn Gly Gln Pro Gly
                   245                 250                 255
Glu Pro Gly Ser Asn Gly Pro Gln Gly Ser Gln Gly Asn Pro Gly Lys
                   260                 265                 270
Asn Gly Gln Pro Gly Ser Pro Gly Ser Gln Gly Ser Pro Gly Asn Gln
                   275                 280                 285
Gly Ser Pro Gly Gln Pro Gly Asn Pro Gly Gln Pro Gly Glu Gln Gly
                   290                 295                 300
Lys Pro Gly Asn Arg Gly Asp Gln Gly Pro Ala Gly Glu Pro Gly Asn
305                 310                 315                 320
Pro Gly Ser Pro Gly Asn Gln Gly Gln Pro Gly Asn Arg Gly Asp Lys
                   325                 330                 335
Gly Ser Pro Gly Asn Pro Gly Gln Pro Gly Asn Glu Gly Gln Pro Gly
                   340                 345                 350
Gln Pro Gly Gln Asn Gly Gln Pro Gly Glu Pro Gly Ser Asn Gly Pro
                   355                 360                 365
Gln Gly Ser Gln Gly Asn Pro Gly Lys Asn Gly Gln Pro Gly Ser Pro
                   370                 375                 380
Gly Ser Arg Gly Asp Gln Gly Ser Pro Gly Asn Gln Gly Ser Pro Gly
385                 390                 395                 400
Gln Pro Gly Asn Pro Gly Gln Pro Gly Glu Gln Gly Lys Pro Gly Asn
                   405                 410                 415
Gln Gly Pro Ala Gly Glu Pro Gly Asn Pro Gly Ser Pro Gly Asn Gln
                   420                 425                 430
Gly Gln Pro Gly Asn Lys Gly Ser Pro Gly Asn Pro Gly Gln Pro Gly
                   435                 440                 445
Asn Arg Gly Asp Glu Gly Gln Pro Gly Gln Pro Gly Gln Asn Gly Gln
                   450                 455                 460
```

-continued

Pro Gly Glu Pro Gly Ser Asn Gly Pro Gln Gly Ser Gln Gly Asn Pro
465                 470                 475                 480

Gly Lys Asn Gly Gln Pro Gly Ser Pro Gly Ser Gln Gly Ser Pro Gly
            485                 490                 495

Asn Gln Gly Ser Pro Gly Gln Pro Gly Asn Pro Gly Gln Pro Gly Glu
        500                 505                 510

Arg Gly Asp Gln Gly Lys Pro Gly Asn Gln Gly Pro Ala Gly Glu Pro
        515                 520                 525

Gly Asn Pro Gly Ser Pro Gly Asn Gln Gly Gln Pro Gly Asn Lys Gly
        530                 535                 540

Ser Pro Gly Asn Pro Gly Gln Pro Gly Asn Glu Gly Gln Pro Gly Gln
545                 550                 555                 560

Pro Gly Gln Arg Gly Asp Asn Gly Gln Pro Gly Glu Pro Gly Ser Asn
            565                 570                 575

Gly Pro Gln Gly Ser Gln Gly Asn Pro Gly Lys Asn Gly Gln Pro Gly
            580                 585                 590

Ser Pro Gly Ser Gln Gly Ser Pro Gly Asn Gln Gly Ser Pro Gly Gln
        595                 600                 605

Pro Gly Asn Pro Gly Gln Pro Gly Glu Gln Gly Lys Pro Gly Asn Arg
        610                 615                 620

Gly Asp Gln Gly Pro Ala Gly Glu Pro Gly Asn Pro Gly Ser Pro Gly
625                 630                 635                 640

Asn Gln Gly Gln Pro Gly Asn Arg Gly Asp Lys Gly Ser Pro Gly Asn
            645                 650                 655

Pro Gly Gln Pro Gly Asn Glu Gln Pro Gly Gln Pro Gly Gln Asn
            660                 665                 670

Gly Gln Pro Gly Glu Pro Gly Ser Asn Gly Pro Gln Gly Ser Gln Gly
        675                 680                 685

Asn Pro Gly Lys Asn Gly Gln Pro Gly Ser Pro Gly Ser Arg Gly Asp
        690                 695                 700

Gln Gly Ser Pro Gly Asn Gln Gly Ser Pro Gly Gln Pro Gly Asn Pro
705                 710                 715                 720

Gly Gln Pro Gly Glu Gln Gly Lys Pro Gly Asn Gln Gly Pro Ala Gly
            725                 730                 735

Glu Pro Gly Asn Pro Gly Ser Pro Gly Asn Gln Gly Gln Pro Gly Asn
            740                 745                 750

Lys Gly Ser Pro Gly Asn Pro Gly Gln Pro Gly Asn Arg Gly Asp Glu
        755                 760                 765

Gly Gln Pro Gly Gln Pro Gly Gln Asn Gly Gln Pro Gly Glu Pro Gly
        770                 775                 780

Ser Asn Gly Pro Gln Gly Ser Gln Gly Asn Pro Gly Lys Asn Gly Gln
785                 790                 795                 800

Pro Gly Ser Pro Gly Ser Gln Gly Ser Pro Gly Asn Gln Gly Ser Pro
            805                 810                 815

Gly Gln Pro Gly Asn Pro Gly Gln Pro Gly Glu Arg Gly Asp Gln Gly
            820                 825                 830

Lys Pro Gly Asn Gln Gly Pro Ala Gly Glu Pro Gly Asn Pro Gly Ser
        835                 840                 845

Pro Gly Asn Gln Gly Gln Pro Gly Asn Lys Gly Ser Pro Gly Asn Pro
        850                 855                 860

Gly Gln Pro Gly Asn Glu Gly Gln Pro Gly Gln Pro Gly Gln Arg Gly
865                 870                 875                 880

Asp Asn Gly Gln Pro Gly Glu Pro Gly Ser Asn Gly Pro Gln Gly Ser
            885                 890                 895

```
Gln Gly Asn Pro Gly Lys Asn Gly Gln Pro Gly Ser Pro Gly Ser Gln
            900                 905                 910
Gly Ser Pro Gly Asn Gln Gly Ser Pro Gly Gln Pro Gly Asn Pro Gly
        915                 920                 925
Gln Pro Gly Glu Gln Gly Lys Pro Gly Asn Arg Gly Asp Gln Gly Pro
    930                 935                 940
Ala Gly Glu Pro Gly Asn Pro Gly Ser Pro Gly Asn Gln Gly Gln Pro
945                 950                 955                 960
Gly Asn Arg Gly Asp Lys Gly Ser Pro Gly Asn Pro Gly Gln Pro Gly
            965                 970                 975
Asn Glu Gly Gln Pro Gly Gln Pro Gly Gln Asn Gly Gln Pro Gly Glu
        980                 985                 990
Pro Gly Ser Asn Gly Pro Gln Gly Ser Gln Gly Asn Pro Gly Lys Asn
        995                1000                1005
Gly Gln Pro Gly Ser Pro Gly Ser Arg Gly Asp Gln Gly Ser Pro
    1010                1015                1020
Gly Asn Gln Gly Ser Pro Gly Gln Pro Gly Asn Pro Gly Gln Pro
    1025                1030                1035
Gly Glu Gln Gly Lys Pro Gly Asn Gln Gly Pro Ala Gly Glu Pro
    1040                1045                1050
Gly Asn Pro Gly Ser Pro Gly Asn Gln Gly Gln Pro Gly Asn Lys
    1055                1060                1065
Gly Ser Pro Gly Asn Pro Gly Gln Pro Gly Asn Arg Gly Asp Glu
    1070                1075                1080
Gly Gln Pro Gly Gln Pro Gly Gln Asn Gly Gln Pro Gly Glu Pro
    1085                1090                1095
Gly Ser Asn Gly Pro Gln Gly Ser Gln Gly Asn Pro Gly Lys Asn
    1100                1105                1110
Gly Gln Pro Gly Ser Pro Gly Ser Gln Gly Ser Pro Gly Asn Gln
    1115                1120                1125
Gly Ser Pro Gly Gln Pro Gly Asn Pro Gly Gln Pro Gly Glu Arg
    1130                1135                1140
Gly Asp Gln Gly Lys Pro Gly Asn Gln Gly Pro Ala Gly Glu Pro
    1145                1150                1155
Gly Asn Pro Gly Ser Pro Gly Asn Gln Gly Gln Pro Gly Asn Lys
    1160                1165                1170
Gly Ser Pro Gly Asn Pro Gly Gln Pro Gly Asn Glu Gly Gln Pro
    1175                1180                1185
Gly Gln Pro Gly Gln Arg Gly Asp Asn Gly Gln Pro Gly Glu Pro
    1190                1195                1200
Gly Ser Asn Gly Pro Gln Gly Ser Gln Gly Asn Pro Gly Lys Asn
    1205                1210                1215
Gly Gln Pro Gly Ser Pro Gly Ser Gln Gly Ser Pro Gly Asn Gln
    1220                1225                1230
Gly Ser Pro Gly Gln Pro Gly Asn Pro Gly Gln Pro Gly Glu Gln
    1235                1240                1245
Gly Lys Pro Gly Asn Arg Gly Asp Gln Gly Pro Ala
    1250                1255                1260

<210> SEQ ID NO 6
<211> LENGTH: 1265
<212> TYPE: PRT
<213> ORGANISM: Artificial
<220> FEATURE:
<223> OTHER INFORMATION: PCM4
```

<400> SEQUENCE: 6

```
Gly Pro Pro Gly Glu Pro Gly Asn Pro Gly Ser Pro Gly Asn Gln Gly
1               5                   10                  15
Gln Pro Gly Asn Arg Gly Asp Lys Gly Ser Pro Gly Asn Pro Gly Gln
            20                  25                  30
Pro Gly Asn Glu Gly Gln Pro Gly Gln Pro Gly Gln Asn Gly Gln Pro
            35                  40                  45
Gly Glu Pro Gly Ser Asn Gly Pro Gln Gly Ser Gln Gly Asn Pro Gly
50                  55                  60
Lys Asn Gly Gln Pro Gly Ser Pro Gly Ser Arg Gly Asp Gln Gly Ser
65                  70                  75                  80
Pro Gly Asn Gln Gly Ser Pro Gly Gln Pro Gly Asn Pro Gly Gln Pro
            85                  90                  95
Gly Glu Gln Gly Lys Pro Gly Asn Gln Gly Pro Ala Gly Glu Pro Gly
            100                 105                 110
Asn Pro Gly Ser Pro Gly Asn Gln Gly Gln Pro Gly Asn Lys Gly Ser
            115                 120                 125
Pro Gly Asn Pro Gly Gln Pro Gly Asn Arg Gly Asp Glu Gly Gln Pro
            130                 135                 140
Gly Gln Pro Gly Gln Asn Gly Gln Pro Gly Glu Pro Gly Ser Asn Gly
145                 150                 155                 160
Pro Gln Gly Ser Gln Gly Asn Pro Gly Lys Asn Gly Gln Pro Gly Ser
            165                 170                 175
Pro Gly Ser Gln Gly Ser Pro Gly Asn Gln Gly Ser Pro Gly Gln Pro
            180                 185                 190
Gly Asn Pro Gly Gln Pro Gly Glu Arg Gly Asp Gln Gly Lys Pro Gly
            195                 200                 205
Asn Gln Gly Pro Ala Gly Glu Pro Gly Asn Pro Gly Ser Pro Gly Asn
            210                 215                 220
Gln Gly Gln Pro Gly Asn Lys Gly Ser Pro Gly Asn Pro Gly Gln Pro
225                 230                 235                 240
Gly Asn Glu Gly Gln Pro Gly Gln Pro Gly Gln Arg Gly Asp Asn Gly
            245                 250                 255
Gln Pro Gly Glu Pro Gly Ser Asn Gly Pro Gln Gly Ser Gln Gly Asn
            260                 265                 270
Pro Gly Lys Asn Gly Gln Pro Gly Ser Pro Gly Ser Gln Gly Ser Pro
            275                 280                 285
Gly Asn Gln Gly Ser Pro Gly Gln Pro Gly Asn Pro Gly Gln Pro Gly
            290                 295                 300
Glu Gln Gly Lys Pro Gly Asn Arg Gly Asp Gln Gly Pro Ala Gly Glu
305                 310                 315                 320
Pro Gly Asn Pro Gly Ser Pro Gly Asn Gln Gly Gln Pro Gly Asn Arg
            325                 330                 335
Gly Asp Lys Gly Ser Pro Gly Asn Pro Gly Gln Pro Gly Asn Glu Gly
            340                 345                 350
Gln Pro Gly Gln Pro Gly Gln Asn Gly Gln Pro Gly Glu Pro Gly Ser
            355                 360                 365
Asn Gly Pro Gln Gly Ser Gln Gly Asn Pro Gly Lys Asn Gly Gln Pro
            370                 375                 380
Gly Ser Pro Gly Ser Arg Gly Asp Gln Gly Ser Pro Gly Asn Gln Gly
385                 390                 395                 400
Ser Pro Gly Gln Pro Gly Asn Pro Gly Gln Pro Gly Glu Gln Gly Lys
            405                 410                 415
```

```
Pro Gly Asn Gln Gly Pro Ala Gly Glu Pro Gly Asn Pro Gly Ser Pro
                420                 425                 430
Gly Asn Gln Gly Gln Pro Gly Asn Lys Gly Ser Pro Gly Asn Pro Gly
            435                 440                 445
Gln Pro Gly Asn Arg Gly Asp Glu Gly Gln Pro Gln Pro Gly Gln
        450                 455                 460
Asn Gly Gln Pro Gly Glu Pro Gly Ser Asn Gly Pro Gln Gly Ser Gln
465                 470                 475                 480
Gly Asn Pro Gly Lys Asn Gly Gln Pro Gly Ser Pro Gly Ser Gln Gly
            485                 490                 495
Ser Pro Gly Asn Gln Gly Ser Pro Gly Gln Pro Gly Asn Pro Gly Gln
                500                 505                 510
Pro Gly Glu Arg Gly Asp Gln Gly Lys Pro Gly Asn Gln Gly Pro Ala
            515                 520                 525
Gly Glu Pro Gly Asn Pro Gly Ser Pro Gly Asn Gln Gly Gln Pro Gly
        530                 535                 540
Asn Lys Gly Ser Pro Gly Asn Pro Gly Gln Pro Gly Asn Glu Gly Gln
545                 550                 555                 560
Pro Gly Gln Pro Gly Gln Arg Gly Asp Asn Gly Gln Pro Gly Glu Pro
            565                 570                 575
Gly Ser Asn Gly Pro Gln Gly Ser Gln Gly Asn Pro Gly Lys Asn Gly
            580                 585                 590
Gln Pro Gly Ser Pro Gly Ser Gln Gly Ser Pro Gly Asn Gln Gly Ser
            595                 600                 605
Pro Gly Gln Pro Gly Asn Pro Gly Gln Pro Gly Glu Gln Gly Lys Pro
            610                 615                 620
Gly Asn Arg Gly Asp Gln Gly Pro Ala Gly Glu Pro Gly Asn Pro Gly
625                 630                 635                 640
Ser Pro Gly Asn Gln Gly Gln Pro Gly Asn Arg Gly Asp Lys Gly Ser
                645                 650                 655
Pro Gly Asn Pro Gly Gln Pro Gly Asn Glu Gly Gln Pro Gly Gln Pro
            660                 665                 670
Gly Gln Asn Gly Gln Pro Gly Glu Pro Gly Ser Asn Gly Pro Gln Gly
        675                 680                 685
Ser Gln Gly Asn Pro Gly Lys Asn Gly Gln Pro Gly Ser Pro Gly Ser
            690                 695                 700
Arg Gly Asp Gln Gly Ser Pro Gly Asn Gln Gly Ser Pro Gly Gln Pro
705                 710                 715                 720
Gly Asn Pro Gly Gln Pro Gly Glu Gln Gly Lys Pro Gly Asn Gln Gly
                725                 730                 735
Pro Ala Gly Glu Pro Gly Asn Pro Gly Ser Pro Gly Asn Gln Gly Gln
            740                 745                 750
Pro Gly Asn Lys Gly Ser Pro Gly Asn Pro Gly Gln Pro Gly Asn Arg
            755                 760                 765
Gly Asp Glu Gly Gln Pro Gly Gln Pro Gly Gln Asn Gly Gln Pro Gly
        770                 775                 780
Glu Pro Gly Ser Asn Gly Pro Gln Gly Ser Gln Gly Asn Pro Gly Lys
785                 790                 795                 800
Asn Gly Gln Pro Gly Ser Pro Gly Ser Gln Gly Ser Pro Gly Asn Gln
                805                 810                 815
```

```
Gly Ser Pro Gly Gln Pro Gly Asn Pro Gly Gln Pro Gly Glu Arg Gly
            820                 825                 830

Asp Gln Gly Lys Pro Gly Asn Gln Gly Pro Ala Gly Glu Pro Gly Asn
        835                 840                 845

Pro Gly Ser Pro Gly Asn Gln Gly Gln Pro Gly Asn Lys Gly Ser Pro
    850                 855                 860

Gly Asn Pro Gly Gln Pro Gly Asn Glu Gly Gln Pro Gly Gln Pro Gly
865                 870                 875                 880

Gln Arg Gly Asp Asn Gly Gln Pro Gly Glu Pro Gly Ser Asn Gly Pro
                885                 890                 895

Gln Gly Ser Gln Gly Asn Pro Gly Lys Asn Gly Gln Pro Gly Ser Pro
            900                 905                 910

Gly Ser Gln Gly Ser Pro Gly Asn Gln Gly Ser Pro Gly Gln Pro Gly
            915                 920                 925

Asn Pro Gly Gln Pro Gly Glu Gln Gly Lys Pro Gly Asn Arg Gly Asp
        930                 935                 940

Gln Gly Pro Ala Gly Glu Pro Gly Asn Pro Gly Ser Pro Gly Asn Gln
945                 950                 955                 960

Gly Gln Pro Gly Asn Arg Gly Asp Lys Gly Ser Pro Gly Asn Pro Gly
                965                 970                 975

Gln Pro Gly Asn Glu Gly Gln Pro Gly Gln Pro Gly Gln Asn Gly Gln
            980                 985                 990

Pro Gly Glu Pro Gly Ser Asn Gly  Pro Gln Gly Ser Gln  Gly Asn Pro
            995                 1000                1005

Gly Lys  Asn Gly Gln Pro Gly  Ser Pro Gly Ser Arg  Gly Asp Gln
    1010                1015                1020

Gly Ser  Pro Gly Asn Gln Gly  Ser Pro Gly Gln Pro  Gly Asn Pro
    1025                1030                1035

Gly Gln  Pro Gly Glu Gln Gly  Lys Pro Gly Asn Gln  Gly Pro Ala
    1040                1045                1050

Gly Glu  Pro Gly Asn Pro Gly  Ser Pro Gly Asn Gln  Gly Gln Pro
    1055                1060                1065

Gly Asn  Lys Gly Ser Pro Gly  Asn Pro Gly Gln Pro  Gly Asn Arg
    1070                1075                1080

Gly Asp  Glu Gly Gln Pro Gly  Gln Pro Gly Gln Asn  Gly Gln Pro
    1085                1090                1095

Gly Glu  Pro Gly Ser Asn Gly  Pro Gln Gly Ser Gln  Gly Asn Pro
    1100                1105                1110

Gly Lys  Asn Gly Gln Pro Gly  Ser Pro Gly Ser Gln  Gly Ser Pro
    1115                1120                1125

Gly Asn  Gln Gly Ser Pro Gly  Gln Pro Gly Asn Pro  Gly Gln Pro
    1130                1135                1140

Gly Glu  Arg Gly Asp Gln Gly  Lys Pro Gly Asn Gln  Gly Pro Ala
    1145                1150                1155

Gly Glu  Pro Gly Asn Pro Gly  Ser Pro Gly Asn Gln  Gly Gln Pro
    1160                1165                1170

Gly Asn  Lys Gly Ser Pro Gly  Asn Pro Gly Gln Pro  Gly Asn Glu
    1175                1180                1185

Gly Gln  Pro Gly Gln Pro Gly  Gln Arg Gly Asp Asn  Gly Gln Pro
    1190                1195                1200

Gly Glu  Pro Gly Ser Asn Gly  Pro Gln Gly Ser Gln  Gly Asn Pro
    1205                1210                1215

Gly Lys  Asn Gly Gln Pro Gly  Ser Pro Gly Ser Gln  Gly Ser Pro
    1220                1225                1230
```

```
Gly Asn Gln Gly Ser Pro Gly Gln Pro Gly Asn Pro Gly Gln Pro
    1235                1240                1245

Gly Glu Gln Gly Lys Pro Gly Asn Arg Gly Asp Gln Gly Pro Ala
    1250                1255                1260

Gly Gly
    1265
```

NON-NATURAL RECOMBINANT GELATINS WITH ENHANCED FUNCTIONALITY

This is a 371 filing based on PCT/NL08/050104 filed Feb. 21, 2008 and claiming priority from European Application No. 07102838.5, filed Feb. 21, 2007; European Application No 07102839.3, filed Feb. 21, 2007; European Application No. 07116189.7, filed Sep. 12, 2007; European Application No. 07116193.9, filed Sep. 12, 2007 and European Application No. 08100556.3, filed Jan. 16, 2008.

FIELD OF THE INVENTION

The invention is in the field of recombinantly produced non natural gelatins and methods of producing these. In particular, the recombinant gelatins have an added functionality and are highly stable, i.e. have a high resistance against proteolytic and/or chemical degradation. The high stability leads to a high yield when produced in recombinant host cells and is also advantageous in the later use of the gelatins, for example in medical compositions or devices.

BACKGROUND OF THE INVENTION

The interest to produce gelatins by recombinant methods is ever increasing. The widespread use and possibilities for use of gelatins in medical and clinical applications poses higher demands on gelatins in every aspect, starting by the need for providing processes that are economically viable to produce gelatins. In turn, this need has prompted careful consideration of process variables and variations in protein sequences that could influence expression properties, and hence yields of desired gelatins that could be obtained.

EP 926543 and Werten et al. 1999 (Yeast 15, 1087-1096) describe a production method of recombinant gelatins, wherein high yields of non-hydroxylated fragments of the helical domain (consisting of Gly-Xaa-Yaa triplet repeats) of mouse type 1 (encoding a 21 kDa and 28 kDa, calculated MW, COL1A1 peptide and a 53 kDa COL1A2) and rat type III (COL3A1) are produced in the methylotrophic yeast Pichia pastoris. A factor such as the fermentation pH was in certain cases found to be of influence on stability of the expressed product, but also the presence proteolytic sequences in the expressed gelatin was found to be relevant and it has been hypothesized that similarity of codon usage with endogenous proteins of the host microorganism could be relevant for obtaining high yields of desired exogenous proteins.

In US 2006/0241032 XRGD-enriched gelatin-like proteins with a minimum (increased) level of XRGD motifs and with a certain distribution of said XRGD motifs are disclosed that were found to be highly suitable for cell adhesion and cell binding in medical and biotechnological applications. The cell binding peptides described therein have good cell attachment properties.

In order to be susceptible for applications of the recombinantly produced gelatins in human beings a lot of effort was directed to make recombinant gelatins as close as possible resembling human gelatin.

However, susceptibility to degradation has been a limiting factor in the ability to produce large amounts of recombinant gelatins.

SUMMARY OF THE INVENTION

The present invention concerns recombinantly produced non-natural gelatins.

In the context of this invention, 'non-natural gelatin' means a polypeptide comprising or consisting of Gly-Xaa-Yaa (GXY) triplets that is artificial, i.e. the amino acid sequence does not occur in nature. Gly, or G, stands for glycine and Xaa and Yaa, or X and Y, stand for any amino acid. Also, the terms "gelatin", "protein", "peptide" and "polypeptide" are used interchangeably herein. Preferably the non-natural gelatins essentially entirely consist of GXY triplets. Similarity with naturally occurring gelatin resides in the presence of a glycine as every third amino acid and the presence of a relatively large proportion of proline residues in the X and Y position, predominantly in the Y position. The present inventors surprisingly found, that the gelatins according to the present invention are secreted by microorganisms in an extremely high yield from over 10 grams per liter (g/l). In order to make the present artificial recombinant gelatin sequences suitable in certain applications the polypeptides were designed to include RGD sequences. Surprisingly it was found that such designed artificial sequences were secreted in high yield from certain microorganisms, remained stable during isolation and purification and that the present gelatins can be used in many applications.

Thus, in one embodiment of the present invention, non-natural or artificial recombinantly produced gelatin polypeptides are provided which comprises at least one RGD sequence.

In another embodiment of the present invention, non-natural recombinantly produced gelatin polypeptides are provided, having a molecular weight of at least 5 kDa.

In one embodiment of the invention in the non-natural recombinantly produced gelatin polypeptides the one or more RGD sequences are not preceded by a proline (P) or hydroxyproline (O). In yet another embodiment of the invention the non-natural recombinantly produced gelatin polypeptides comprise one or more XRGD motifs, wherein X is selected from the group consisting of D, Y, W, F, C, M, K, L, I, R, H, S, T, V, A, G, N, Q and E. In terms of stability of the polypeptide it is advantageous to avoid the presence of aspartic acid (D) before the arginine (R) in the arginine-glycince-aspartic acid (RGD) motif, hence in one embodiment of the invention in the non-natural recombinantly produced gelatin polypeptides the one or more RGD sequences are not preceded by a aspartic acid (D). In one embodiment X is selected from the group consisting of K, R, H, S, A, G, N, Q and E. In one embodiment X is selected from the group consisting of K, S, A, G, N, Q and E. In terms of yield obtained, it is advantageous to include an ERGD motif in the non-natural gelatin, thus in one embodiment the non-natural recombinantly produced gelatin polypeptides comprise one or more ERGD motifs.

Furthermore, it was found that it is advantageous in various applications and that its utility could be improved significantly in gelatins that are enriched in RGD sequences. A definition of RGD-enriched is given below, however it is for example preferred for a gelatin with a length of about 300 amino acids, to comprise at least 2 RGD motifs, preferably at least 3 RGD or at least 4 or more RGD motifs.

In one specific embodiment, the non natural recombinant gelatins comprise less than 10% hydroxyproline or less than 1% or the hydroxyproline is completely absent.

In still another embodiment of the present invention, a non-natural recombinantly produced gelatin polypeptide is provided comprising or consisting of at least two repeats, e.g. a multimer, of the recombinant gelatin polypeptide (monomer) as described above. It is preferred that the repeats are preferably identical and it is also preferred that there are no intervening amino acids between the monomers, or monomeric repeat units.

The stability and expression level of gelatin-like sequences (and variants thereof and fragments of any of these) is on a high level by expressing the non-natural sequences as described above in micro organisms and these polypeptides are secreted by the selected micro organisms in high yields. Especially suitable microorganisms are methylotrophic yeasts, which are modified by the engineered nucleic acid sequences (DNA or RNA). By using these modified yeasts large scale fermentations can be used producing the artificial RGD comprising recombinant gelatin at high yields.

Also compositions and devices consisting of or comprising the present artificial RGD containing recombinant gelatins are provided.

GENERAL DEFINITIONS

Whereas often the terms 'collagen', 'collagen-related', 'collagen-derived' or the like are also used in the art, the term 'gelatin' or 'gelatin-like' protein will be used throughout the rest of this description. Natural gelatin is a mixture of individual polymers with MW's ranging from 5,000 up to more than 400,000 daltons.

The terms "cell adhesion" and "cell attachment" are used interchangeably.

Also the terms "RGD sequence" and "RGD motif" and "Arg-Gly-Asp" are used interchangeably. The term "RGD-enriched" refers herein to amino acid sequences comprising at least one RGD motif. The term "RGD-enriched" in the context of this invention means that a certain level of XRGD motifs, calculated as a percentage of the total number of amino acids per molecule is present and that there is a certain more or less even distribution of RGD sequences in the amino acid sequence. The level of RGD sequences can be expressed as a percentage. This percentage is calculated by dividing the number of RGD motifs by the total number of amino acids and multiplying the result with 100. Also, the number of XRGD motifs is an integer starting from 1, 2, 3, . . . etc.

In particular "RGD-enriched" refers herein to amino acid sequences wherein the percentage of RGD motifs related to the total number of amino acids is at least 0.4 and if the amino acid sequence comprises 250 amino acids or more, each stretch of 250 amino acids contains at least one XRGD motif. Preferably the percentage of XRGD motifs is at least 0.6, more preferably at least 0.8, more preferably at least 1.0, more preferably at least 1.2, more preferably at least 1.5 and most preferably at least 1.8. Preferably "RGD-enriched" refers to polypeptides having at least one RGD sequence per 5 kDa of molecular weight. In the context of the present invention the molecular weight refers to the calculated molecular weight, in particular of the primary amino acid sequence, thus not taking into account possibly post-translational modifications of the particular host-micro-organism wherein the present polypeptides were recombinantly produced. It is noted that of the preferred micro-organisms herein indicated, in particular yeasts, it is assumed no post-translational modifications occur. It is preferred the present gelatins do not contain a part of 5 kDa without an RGD sequence.

A percentage RGD motifs of more than at least 0.4 corresponds with more than at least 1 RGD sequence per 250 amino acids. The number of RGD motifs is an integer, thus to meet the feature of 0.4%, an amino acid sequence consisting of 251 amino acids should comprise at least 2 RGD sequences. Preferably the RGD-enriched recombinant gelatins of the invention comprise at least 2 RGD sequences per 250 amino acids, more preferably at least 3 RGD sequences per 250 amino acids, most preferably at least 4 RGD sequences per 250 amino acids. In a further embodiment an RGD-enriched gelatin according to the invention comprises at least 4 RGD motifs per calculated molecular weight of 30 kD, preferably at least 6 RGD motifs per 30 kD.

"A relatively large proportion of proline residues in the X and Y position" means that at least one third of the GXY triplets contains a proline residue.

A "fragment" is a part of a longer nucleic acid or polypeptide molecule, which comprises or consist of e.g. at least 10, 15, 20, 25, 30, 50, 100, 200, 500 or more consecutive nucleotides or amino acid residues of the longer molecule.

"Native" or "natural" collagens or collagenous domains refer to those nucleic acid or amino acid sequences found in nature, e.g. in humans or other mammals.

A "non-natural gelatin" or engineered recombinant gelatin, or artificial recombinant gelatin is a GXY sequence that is not or is not part of a naturally occurring collagen.

The terms "protein" or "polypeptide" or "peptide" are used interchangeably and refer to molecules consisting of a chain of amino acids, without reference to a specific mode of action, size, 3-dimensional structure or origin. An isolated protein is a protein not found in its natural environment, such as a protein purified from a culture medium.

The term "support" or "cell attachment support" refers herein to any support which can be used to facilitate cell attachment and/or growth, such as culture dishes, microcarriers (e.g. microcarrier beads), stents, implants, plasters, etc.

The term "substantially identical", "substantial identity" or "essentially similar" or "essential similarity" means that two polypeptide, when aligned pairwise using the Smith-Waterman algorithm with default parameters, comprise at least 60%, 70%, 80%, more preferably at least 90%, 95%, 96% or 97%, more preferably at least 98%, 99% or more amino acid sequence identity. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or using in EmbossWIN (e.g. version 2.10.0). For comparing sequence identity between two sequences, it is preferred that local alignment algorithms are used, such as the Smith Waterman algorithm (Smith T F, Waterman M S (1981) J. Mol. Biol 147(1); 195-7), used e.g. in the EmbossWIN program "water". Default parameters are gap opening penalty 10.0 and gap extension penalty 0.5, using the Blosum62 substitution matrix for proteins (Henikoff & Henikoff, 1992, PNAS 89, 915-919).

The term "comprising" is to be interpreted as specifying the presence of the stated parts, steps or components, but does not exclude the presence of one or more additional parts, steps or components.

In addition, reference to an element by the indefinite article "a" or "an" does not exclude the possibility that more than one of the element is present, unless the context clearly requires that there be one and only one of the elements. The indefinite article "a" or "an" thus usually means "at least one".

"Monomer" refers to a polypeptide unit (or nucleic acid sequence encoding it) which can be used to generate a "multimer" (or "polymer", which is used interchangeably) by repeating the unit in a linear fashion to generate a longer polypeptide. The monomer units are preferably repeated without intervening amino acids, although optionally 1, 2, 3, 4, 5 or more linking amino acids may be present between monomer units.

The term "improved stability" means that a gelatin is not hydrolysed or is hydrolysed to a lesser extent, preferably by at least 10% or higher, under usual culture conditions of the yeast expression host and usual conditions under which gelatins are isolated compared to the corresponding sequences derived from natural occurring structures.

"Free of triple helix" structure refers to essentially the absence of the positive peak characteristic of the collagen triple helix in a circular dichroism spectrum. Circular dichroism spectrometry can be carried out as described in Werten et al. (2001, Protein Engineering 14:447-454).

DETAILED DESCRIPTION OF THE INVENTION

It was found, surprisingly, that it is possible to obtain high yields of improved, highly stable peptides or polypeptides. This is of great benefit to render the production process of recombinant gelatins economically viable. The instant invention thus concerns recombinantly produced non-natural gelatins. The stability of the present gelatins is beneficial for all applications, in particular for applications that rely on the integrity of the gelatins. The polypeptides also do not display any health related risks, as they have a low antigenicity meaning that these polypeptides can be used without the risk of transferring pathological factors such as viruses, prions and the like. The present invention is directed to peptides, polypeptides or proteins, in particular to gelatins or gelatin-like proteins, which are highly suitable to be used in clinical, medical and/or biotechnological applications. For example the use as a plasma expander whereby intact molecules are kept in circulation is of interest and an application for which the present gelatins are advantageously suited. Also in particular haemostats, dermal filler or cell adhesion are area's of interest. In one embodiment the invention is directed to cell binding peptides or polypeptides that have improved properties compared to known recombinant gelatin-like RGD-comprising polypeptides, such as described in US 2006/0241032, in particular the sequence designated as SEQ ID NO: 2 therein.

As explained due to the implicit presence of glycine residues in gelatins and the relatively large proportion of proline residues, a non-natural gelatin-like polypeptide or protein according to the present invention may have a certain degree of homology with polypeptide sequences of the same length which are part of natural collagen. The present gelatins as such however do not occur in nature, e.g. are different form natural sequences. It is also possible, that the amino acid sequence exhibits more than 50% homology with a native collagen amino acid sequence, or 60%. The difference may reside in mutations of native sequences such as insertions, deletions and substitutions vis a vis the native sequence. Besides, use can be made of synthetic DNA sequences with a the appropriate degree of homology with native DNA sequences. The mutations should always result in an amino acid sequence with more than 4 different amino acids, two of them being Gly and Pro. Preferably more than 8, even more than 9 different amino acids should be present. The majority of triads of amino acids, preferably at least 80%, should have the sequence GXY, wherein G is glycine and X and Y are any amino acid, but an occasional deviating triad such as AXY (A=alanine) does not alter the required properties. A substantial number of GXY triplets should have the sequence GXP or GPY (P=proline), preferably more than half of the GXY triplets contains a proline residue. Preferably cysteine is avoided.

Preferably proline is not hydroxylated, resulting in non-gelling polypeptides.

In one aspect of the invention the non-natural gelatin polypeptides are more hydrophilic than natural gelatin. For example, the polypeptides have a GRAVY value (Grand average of hydrophilicity; Kyte and Doolittle 1982, J. Mol. Biol. 157, 105-132) of less then −1.4, such as less than or equal to −1.5, −1.6, −1.7 −1.8, −1.9, etc. Hydrophilicity can be increased by reducing the percentage of hydrophobic amino acids in the sequence (such as Trp, Tyr, Phe, Leu, Ile, Val and Met). E.g. the monomer and/or multimer polypeptides may comprise less than 3, 2, or 1, most preferably 0 of the mentioned hydrophobic amino acids, other than Proline and Glycine. Also, the monomer and/or multimer may comprise a high amount of hydrophilic amino acids, such as Asparagine (Asn) and/or Glutamine (Gln). In one embodiment the present polypeptides comprise at least 10% Asn (N) residues, or at least 10% Gln (Q) residues, or at least 20% of N+Q residues, preferably at least 10% N and at feast 10% Q residues. Said percentage is the number of N and/or Q residues divided by the total number of amino acid residues of the polypeptide multiplied by 100.

According to the invention gelatins are provided with excellent cell attachment properties and which comprise advantages such as improved stability, improved cell attachment and tissue support properties, probably due to the improved stability.

In one embodiment the non-natural recombinantly produced gelatin-like polypeptide has at least 60% sequence identity to SEQ ID NO:1. This sequence is also referred to herein as PCM-monomer.

In one embodiment the present gelatin polypeptide can also be defined as a protein comprising or consisting of an amino acid sequence having at least 70%, preferably at least 80%, 90% or more amino acid sequence identity SEQ ID NO: 1 or to a fragment thereof such as a fragment of at least 15 consecutive amino acids, more preferably at least 92%, 95%, 96%, 98%, 99% sequence identity or more. "Fragments" are parts of less than 1000 amino acids, such as 800, 600, 500, 300, 250, 200, 100, 50, 30 or less consecutive amino acids, but preferably at least 10, 15 or 20 amino acids.

Gelatin-Like Polypeptide Monomers According to the Invention

In one embodiment the present invention provides non-natural recombinantly produced gelatin polypeptides which have a molecular weight of at least 5 kDa and which comprise at least one RGD sequence per 5 kDa of molecular weight. Preferably the gelatin polypeptides have a molecular weight of at least 15 kDa, preferably at least 20 kDa and more preferably at least 25 kDa calculated molecular weight and preferably each part of the gelatin of 5 kDa comprises at least one RGD sequence. Preferably the molecular weight is less than 200 kDa, more preferably less than 150 kDa. Such gelatins were found to have an even improved stability.

Especially stability and yield of full length, non-degraded RGD enriched protein in methylotrophic yeasts (especially of the genus *Pichia* or *Hansenula*) could be improved by expressing a nucleic acid sequence encoding an RGD-enriched gelatin like polypeptide.

In one embodiment of the invention a non-natural recombinantly produced gelatin polypeptide monomer is provided, which has a molecular weight of at least 5 kDa which comprises at least one XRGD motif, wherein X is any amino acid with the exception of D (Asp) and P (Pro) or O (hydroxyproline), and preferably each part of the gelatin of 5 kDa comprises at least one XRGD sequence.

Thus a preferred in one embodiment the invention concerns a non-natural recombinantly produced gelatin polypeptide having a molecular weight of at least 5 kDa, wherein at least 80% of the amino acids are present as Gly-Xaa-Yaa triplets, wherein G is glycine and Xaa and Yaa are any amino acid, said polypeptide comprising at least one XRGD motif per 5 kDa of molecular weight, wherein X is any amino acid with the exception of D (Asp) and P (Pro) or O (hydroxyproline).

In order to obtain the present non-natural polypeptides, for example nucleic acid sequences encoding natural gelatin sequences may be started from which may be modified by site directed mutagenesis to result in sequences having XRGD motifs as defined herein. Of course it is also possible to simply design amino acid sequences comprising consecutive GXY motifs, such as at least 5, 10, 15, 20, 30, 50, 100, 200, 300 or more consecutive GXY motifs, whereby at least one, but preferably more XRGD motifs are included in the sequence. Such designed polypeptides can be made by making nucleic acid sequences encoding these (using routine molecular biology techniques) and expressing these in a recombinant host cell. Preferably the spacing of the XRGD motifs (with X not being D or P or O) is such that at least about 0, 10, 15, 20, 25, 30 or more intervening amino acids are present. When several XRGD-motifs are present in the sequence, these can be spaced regularly or irregularly, depending on the application under consideration.

Preferably, the XRGD motifs are part of the GXY motifs, i.e. the sequence of GXY triplets is not disrupted by the XRGD motif(s). For example in a sequence -GXY-GXY-GXR-GDY-GXY-GXY- the XRGD motif does not disrupt the consecutive GXY triplets.

Thus, also more than 2 XRGD motifs may be present in the monomer polypeptide, such as 3, 4, 5, 6 or more, wherein X is again any amino acid, but preferably not D, P or O. Such further XRGD motifs can also be introduced into natural sequences, e.g. by site directed mutagenesis or using other methods.

In a further embodiment the invention relates to recombinant gelatins which are not glycosylated. Glycosylation should be preferably prevented for applications where no immune response is desired. In a preferred embodiment, the non-natural recombinant gelatin polypeptides according to the invention do not comprises threonine (Thr, T). It is believed that the absence of threonine in the amino acid sequence may be an effective way to prevent the glycosylation in biotechnological production systems using for instance yeast cell cultures.

The monomer may comprise additional amino acids at one or both ends, e.g at the N- and/or C-terminal. For example, 1, 2, 3, 6, 9, 12, 15 or more amino acids may be present. These may be in the form of GXY triads. Additional amino acids at the termini, in particular the C-terminus, enhance the stability of the recombinant gelatins, for example by preventing C-terminal degradation such as one by one cleavage of amino acids. Also additional amino acids at the termini facilitates multimer construction, the multimeric recombinant gelatin polypeptide may comprise N-terminal and C-terminal amino acids that are not part of the repeating amino acid sequence. In one embodiment the recombinant gelatins according to the present invention, are preceded by a glycine-proline-proline (GPP) triplet and extended with two glycine residues (GG) at the carboxy-terminus.

The above described polypeptides according to this invention have a good stability to enzymatic and/or chemical proteolysis breakdown.

Preferably no or reduced degradation or cleavage products, i.e. polypeptides of a smaller size than that of the encoded (full length) polypeptide, are seen in/after a stability assay, e.g. on SDS-PAGE gels or by other methods such as LC-MS. Stability can for example be tested after the polypeptide is secreted into the culture medium of the yeast host, whereby the polypeptide is stable if substantially all (at least 95%, preferably at least 98%, 99% or most preferably 100%) of the recombinant polypeptide is full size. Stability to enzymatic or chemical hydrolysis can be also be tested by incubating the polypeptide with one or more proteolytic enzymes or hydrolytic chemicals and by analysing the resulting molecular weight after a specified period of treatment.

For example, when the molecular weight of recombinant natural gelatins and gelatins according to the invention produced in the same yeast host is compared after fermentation, the recombinant gelatin according to the invention is less degraded than the natural gelatin produced under the same conditions and in the same way. Degradation can also be quantified, e.g. by analysing band intensities on SDS-PAGE gels loaded with the same amount of sample. See e.g. Werten et al. 1999 (supra).

In a preferred embodiment the non-natural recombinantly produced gelatin polypeptide is prepared by recombinant DNA technology, especially by expression of nucleic acid sequences in methylotrophic yeast, preferably *Pichia* and/or *Hansenula*, most preferably *Pichia pastoris*. The host is preferably not capable of hydroxylating praline, i.e. it lacks a functional prolyl-4-hydroxylase, so that in the resulting polypeptide less than 10%, more preferably less than 5%, less than 4%, less than 3 or 2%, most preferably less than 1% of the proline residues of the GXY triplets and/or of the total proline residues in the polymer are hydroxylated. Preferably, the prolines are not hydroxylated. In another preferred embodiment of this invention the prolines are hydroxylated so more than 10% or more than 20, 30, 40, 50% or more is hydroxylated. Recombinant gelatins of this invention can be derived from natural collagenous sequences, with further modification to fulfill the amino acid sequence criteria described elsewhere herein.

Gelatin-Like Polypeptide Multimers According to the Invention

In a further embodiment multimers of the above monomers are provided. Such multimers thus comprise or consist of at least 2, 3, 4, 5, 6, 7, 8, 9 or 10 repeats of the monomer sequence. Thus, in a further embodiment a recombinant gelatin polypeptide is provided comprising or consisting of a multimer of a monomer sequence described above. Preferably, the monomer repeats are repeats of the same monomer unit (having identical amino acid sequences), although optionally also combinations of different monomer units (having different amino acid sequences, each falling under the criteria above) may be used.

Preferably the monomer units are not separated by spacing amino acids, although short linking amino acids, such as 1, 2, 3, 4 or 5 amino acids, may also be inserted between one or more of the monomers.

In one embodiment the multimers comprise or consist of at least 2, 3, 4, 5, 6, 7, 8, 9 or 10 repeats of a monomer as described above. In one embodiment the multimers comprise or consist of at least 2, 3, 4, 5, 6, 7, 8, 9 or 10 repeats of a sequence having at least 60%, preferably at least 70%, 80%, 90% or more amino acid sequence identity or is substantially identical to SEQ ID NO: 1 or a fragment thereof. In one embodiment the multimer recombinant gelatins according to the present invention, are preceded by a glycine-proline-proline (GPP) triplet and extended with two glycine residues (GG) at the carboxy-terminus. Thus recombinant gelatins according to the present invention include GPP((SEQ ID NO: 1))$_x$GG wherein x is an integer selected of 2 and higher, preferably x is 2 or 3 or 4 or 5 or 6 or 7 or 8, up to and including 10 or more. For x=1 a gelatin according to the present invention called PCM (SEQ ID NO: 2) is obtained. Two repeats of the PCM monomer results in the PCM-dimer (SEQ ID NO: 3); in above formula for x=2 the sequence PCM2 (SEQ ID NO: 4) is obtained and four repeats of the PCM monomer results in the PCM-tetramer (SEQ ID NO: 5); in above formula for x=4 the sequence PCM4 (SEQ ID NO: 6) is obtained.

Such multimers can be generated using known standard molecular biology methods.

Material and Compositions Comprising the XRGD-Comprising Monomers and/or Multimers The present invention is directed to peptides, polypeptides or proteins, in particular to recombinant gelatins or gelatin-like proteins, which are highly suitable for cell adhesion and can be used in medical or biotechnological applications.

It was found that recombinant gelatins according to the invention are very suitable for coating cell culture supports which can be used in biotechnological processes or in medical applications.

RGD sequences in gelatins can adhere to specific receptors on the cell wall called integrins. These integrins differ in their specificity in recognising cell binding amino acid sequences. Although both natural gelatin and, for example, fibronectin may contain RGD sequences, gelatin can bind cells that will not bind to fibronectin and vice versa. Therefore fibronectin comprising RGD sequences cannot always replace gelatin for cell adhesion purposes.

Recombinantly produced gelatin does not suffer from the disadvantage of animal-derived gelatin, i.e. potential contamination with pathogens originating from the animal from which the gelatin was derived.

When used as or in combination with a cell culture support, the gelatin-like polypeptides according to the invention functions as a cell binding polypeptide. It has the advantage over other polypeptides that it can also be metabolised by the cells growing on it.

A further advantage of recombinantly produced gelatins is that the molecular weight (MW) can be kept uniform. Natural gelatins, in particular gelatins isolated form natural sources, unavoidably have a broad molecular weight distribution with peptides smaller than 5 kDa up to large polymers with a molecular weight larger than 400 kDa, resulting from the production method. In particular in combination with microcarrier core beads as cell culture support, a disadvantage of smaller peptides is that they will adhere inside finer pores of the microcarrier which cannot be reached by the cells so that part of the added gelatin is not used. With recombinant production methods the gelatin can be designed with the desired molecular weight, preventing this undesired loss of material.

A cell support comprising a recombinant gelatin according to the invention is provided. Such a cell support may be selected from the group consisting of 1) a cell-culture support, such as a core head (e.g. a microcarrier bead) or a Petri dish or the like, coated with one or more gelatin-like polypeptides according to the invention;
2) an implant or transplant device (such as hip-, dental-, or other implants, stents, etc.) coated with one or more of the recombinant gelatins according to the invention,
3) a scaffold or matrix for tissue engineering, such as artificial skin matrix material, coated with one or more recombinant gelatin like polypeptides;
4) a wound healing product coated with one or more recombinant gelatin like polypeptides;
5) a tissue adhesive comprising or consisting of one or more recombinant gelatin like polypeptides;

In one embodiment the cell supports provided herein are preferably comprise only one recombinant gelatin according to the invention, i.e. selected from one of the polypeptides provided. The product is thus uniform in amino acid sequence, molecular weight, etc. Optionally the peptides may be cross-linked by e.g. chemical cross-linking.

In a different embodiment mixtures of polypeptides according to the invention may be used, such as 2, 3, 4, 5, or more different amino acid sequences according to the invention. The ratios of mixtures may vary, such as 1:1, or 10:1, 50:1, 100:1, 1:100, 1:50, 1:10, and ratios in between these. Optionally also these mixtures or parts thereof may be crosslinked by e.g. chemical cross linking.

When using the recombinant gelatin monomer(s) and/or multimers for coating porous microcarrier beads, preferably polypeptides with a molecular weight of at least about 30 kDa are used, e.g. at least about 30 kDa, 40 kDa, 50 kDa, 60 kDa or 70 kDa or more. The reason for this is that smaller polypeptides enter the pores, thereby not contributing to the cell attachment properties of the coated beads and the coating process may be inefficient, especially if low concentrations of polypeptides are used in the process.

Preferably the molecular weight of the gelatin or gelatin-like protein used is uniform, with more than 75%, preferably more than 85%, more preferably more than 95% or even at least 98% of the gelatin or gelatin-like protein having a uniform MW within 20% from the selected molecular weight.

By selecting a molecular weight, within the above specified range, in a coating process the viscosity of the gelatin or gelatin-like protein coating solution can be accurately controlled. Complete or, more important, partial gelling of such a gelatin solution can be prevented while being able to select a high as possible concentration of the gelatin. The uniform gelatin ensures a process of identically coated microcarriers. The uniform coating process allows the use of a minimum amount of gelatin and the use of a minimum volume of gelatin coating solution. All this results in a far more efficient coating process than that is known in the art.

In one embodiment of the invention non-porous core beads are coated with gelatin of the invention. Suitably non-porous core beads are made of polystyrene or glass. Other suitable non-porous materials are known to those skilled in the art.

A particular advantageous embodiment is the process of the invention wherein porous core beads, such as beads from modified dextran or cross-linked cellulose, or (porous) polystyrene, in particular DEAE-dextran, are coated with gelatin of the invention. Other suitable porous materials are known to those skilled in the art, and include e.g. other chemically modified or non-modified polysaccharides.

The size of the beads may vary from 50 μm to 500 μm. Typical mean microcarrier bead sizes are about 100, about 150 or about 200 μm in physiological saline. Size ranges with at least 90% of the beads lying within the range may vary from 80-120 μm, 100-150 μm, 125-175 μm or 150-200 μm.

A wide range of cells may be cultured on microcarriers. For instance, cells from invertebrates, from fish, birds and cells of mammalian origin may be cultivated on microcarriers. Transformed and normal cell lines, fibroblastic and epithelial cells and even genetically engineered cells may be cultivated on microcarriers for various biological applications such as for the production of immunologicals like interferons, interleukins, growth factors etc. Cells cultured on microcarriers also serve as hosts for a variety of viruses that are used as vaccines like foot and mouth disease or rabies.

Microcarrier cultures have a wide number of applications other than mass cultivation as well. Cells rowing on microcarriers serve as an excellent tool for studying different aspects of cell biology such as cell-to-cell or cell-to-substratum interactions. Cell differentiation and maturation, metabolic studies may also be carried out using microcarriers. Such cells can also be used for electron microscopic studies or for the isolation of cell organelles such as the cell membrane. Also, this system is essentially a three-dimensional system and serves as a good 3-D model. Similarly, co-cultivation of cells can be done using this system. Thus applications include the production of large quantities of cells, viruses and cell products (e.g. interferon, enzymes, nucleic acids, hormones), studies on cell adhesion, differentiation and cell function, perfusion column culture systems, microscopy studies, harvesting mitotic cells, isolation of cells, membrane studies, storage and transport of cells, assays involving cell transfer and studies on uptake of labeled compounds.

Microcarriers may also be used for the depletion of macrophages from a population of spleen cells. DEAE-dextran microcarriers coated with the recombinant non natural gelatin of this invention can potentiate stimulation of lymphocytes by concanavalin A (con A). Microcarrier beads confluent with allogenic tumour cells can be injected in mice to increase humoral and cell-mediated immunity. Plant protoplasts can be immobilised on DEAE-dextran microcarriers coated with the recombinant gelatins of this invention.

As a result of the large surface area to volume ratio provided by microcarriers, they can successfully be used for a variety of biological productions on a laboratory scale as well as an industrial scale of for instance even 4000 liters or more.

Large scale production of expressed products can be accomplished with gelatin-coated microcarriers. Loading of microcarriers in production scale bioreactors is generally 20 g/l, but may be increased up to 40 g/l. Microcarriers may be used in batch and perfusion systems, in stirred cultures, and wave bioreactors, as well as to increase the surface area of traditional stationary monolayers and roller cultures.

In a further preferred embodiment the non-natural gelatin polypeptide is in essence free of hydroxyproline residues. Hydroxylation is a requirement for the formation of triple helices in collagen and plays a role in gelation of gelatin. In particular less than 5%, more preferably less than 3% of the amino acid residues of the recombinant gelatins are hydroxyprolines, more preferably less than 1%, and most preferably the recombinant gelatin is free from hydroxyprolines in applications where the gelling capability of the recombinant gelatin is unfavorable. The hydroxyproline-free recombinant gelatins can be used in higher concentrations, and the solutions will be less viscous requiring less vigorous agitation, resulting in less shear forces on the cultured cells. As described in WO 02/070000 A1, recombinant gelatins which are in essence free from hydroxyprolines do not show immune reactions involving IgE in contrast to natural gelatin. Absence of hydroxyprolines can for example be achieved by expression in *Pichia* hosts, such as *Pichia pastoris*, which has not been transformed with or does not comprise a functional prolyl-4-hydroxylase enzyme.

The amount of hydroxyprolines can be determined by any standard aminoacid analysis method like, for example, described in HP AminoQuant Series II, operators handbook, 1990, Hewlett-Packard GmbH, Federal Republic of Germany, Waldbronn Analytical Division, HP Part No. 01090-90025.

In one embodiment the present recombinantly produced non-natural gelatin polypeptides are free of triple helix structure.

A process for the preparation of collagen coated microcarriers is described in U.S. Pat. No. 4,994,388. In short providing a core bead with a collagen coating is performed in two steps: coating and fixing. The core beads are suspended in an acidic, aqueous collagen solution (0.01-0.1N acetic acid), and the solution is evaporated to dryness. The dry, collagen-coated beads are then suspended in a solution which contains a protein cross-linking agent such as glutaraldehyde, thus cross-linking the collagen coating. Alternatively, the core beads wetted with the collagen solution are not dried entirely before the start of the fixing step. Variations in coating conditions and alternative coating processes are well within the competence of those skilled in the art.

In a further embodiment the invention relates to the use of recombinant gelatins according to the invention to block surface receptors on cells and to make compositions for blocking such receptors. Blocking of receptors of cells is applied in for example inhibiting angiogenesis or in blocking integrins on cardiac fibroblasts.

Cell supports coated with recombinant gelatin according to the invention, on which cells have been grown can be applied during, for example, transplantation of skin or wound treatment or to enhance bone or cartilage (re)growth. It is also possible to coat implant materials with recombinant gelatin of the invention to adhere cells which promote implantation.

In one embodiment the presents inventions concerns a composition comprising a non-natural recombinantly produced gelatin polypeptide according to the present invention.

In one embodiment the composition is a pharmaceutical composition or a nutritional- or nutraceutical composition. For example the present polypeptides, in particular the multimers, can be used as a plasma expander in blood substitute liquids.

In yet another embodiment of the invention a controlled release composition comprising one or more recombinant gelatins according to the invention is provided. The composition may, thus further comprise one or more drugs. Controlled release formulations can be made as known in the art, for example by using the recombinant gelatin-like proteins or compositions comprising these as a coating layer surrounding one or more drugs or for making a matrix in which the drug is enclosed or incorporated. The controlled release composition can be administered by injection (subcutaneous, intravenous or intramuscular) or orally or via inhalation. However, the used controlled release composition can also be implanted via surgery. Yet another suitable route of administering is via an external wound dressing or even transdermally.

The controlled release composition preferably comprises the recombinant gelatin in a cross-linked form, e.g. chemically crosslinked. The invention further provides use of a controlled release composition as described herein for the preparation of a medicament for the treatment of pain, cancer therapy, cardiovascular diseases, myocardial repair, angiogenesis, bone repair and regeneration, wound treatment, neural stimulation/therapy or diabetics.

In yet another embodiment of this invention the non natural recombinant gelatins of this invention are used as wound dressing and or hemostats. For this the recombinant gelatin of this invention is transferred into a sponge like material using known techniques in the art. The sponge can be impregnated with suitable anti bleeding compounds. Furthermore the recombinant gelatin sponge can be combined with other sponge like material or the sponge can be made by evaporation of a water solution of the recombinant gelatin of this invention in which the solution can comprise other components to improve sponge properties, like adhesion to the wound, blood take up capacity and the like. Suitable compounds to combine with the recombinant non natural gelatins of this invention are for example chitosan or oxidized regenerated cellulose (ORC). Optionally the recombinant gelatin of this invention is crosslinked to some extend during or after the sponge formation.

This crosslinking is done by any method known in the art. One example is to add a crosslinking agent to the solution of the recombinant gelatin of this invention in water, after which the water is evaporated. The crosslinking agent can also be added after the sponge material is formed by impregnating the sponge with the crosslinking material and evaporating the sponge to dryness. Suitable crosslinking agents are for example aldehydes, like glutaraldehyde or a carbodiimide.

The medical field of indications for the sponge according to the invention is rather broad. The sponge not only can be used for stopping bleeding in very large hemorrhaging areas with a high blood pressure, but also for stopping oozing bleeding. The following internal or external surgical procedures are successfully carried out using the hemostatic sponge according to the invention: general surgery, for instance surgery of parenchymatous organs (liver, kidney, spleen, etc.), cardiovascular surgery, thoracic surgery, transplantation surgery, orthopedic surgery, bone surgery, plastic surgery, ear, nose and throat surgery, neurosurgery, surgery in urology and gynecology as well as haemostasis, such as in wound treatment.

In yet another embodiment, the non-natural recombinant gelatin of this invention is used as a dermal filler. In this application, the non natural recombinant gelatins are first dissolved in water and than precipitated from the water solution by adding a less hydrophilic solvent like for example acetone. During the preparation a crosslinking agent may be present like for example glutaraldehyde, which crosslinks two lysine residues. Another well known biocompatible crosslinker is 1-ethyl-3-(3-dimethylaminopropyl)carbodiimide hydrochloride; EDC.

These crosslinkers or combination of crosslinkers can comprise agents that start crosslinking spontaneously upon addition to polypeptide solution, or after adjusting for example, pH, or by photo initiation or other activation mechanisms.

Suitable crosslinking agents are preferably those that do not elicit toxic or antigenic effects when released during biodegradation. Suitable crosslinking agents are, for example, one or more of glutaraldehyde, water-soluble carbodiimides, bisepoxy compounds, formalin, 1-ethyl-3-(3-dimethylaminopropyl) carbodiimide, N-hydroxy-succinimide, glycidyl ethers such as alkylene glycol diglycidyl ethers or polyglycerol polyglycidyl ether. Very small particles can be obtained. The recombinant collagen particles can have an average size of from 1 to 500 micron. and are suitable as injectable tissue fillers or for tissue augmentation or cosmetic surgery. For such applications the average particle size is preferably more than or equal to 100 micron. Average particle sizes of 150 to 500 are also preferred. Other suitable average particle sizes are 220, 250, 300, 350, 400 and 450 micron. Particles suitable as tissue fillers or augmentors should be deformable so that no lump formation occurs, but a natural impression is obtained after injection of the particles.

The recombinant gelatins according to the invention can be produced by recombinant methods as disclosed in EP-A-0926543, EP-A-1014176 or WO01/34646. Also for enablement of the production and purification of gelatins of the invention reference is made to the examples in EP-A-0926543 and EP-A-1014176.

Thus the non-natural gelatin polypeptides can be produced by expression of nucleic acid sequence encoding such polypeptide by a suitable micro-organism. The process can suitably be carried out with a fungal cell or a yeast cell. Suitably the host cell is a high expression host cells like *Hansenula, Trichoderma, Aspergillus, Penicillium, Saccharomyces, Kluyveromyces, Neurospora* or *Pichia*. Fungal and yeast cells are preferred to bacteria as they are less susceptible to improper expression of repetitive sequences. Most preferably the host will not have a high level of proteases that attack the collagen structure expressed. The use of methylotrophic yeast cells is preferred. In this respect *Pichia* or *Hansenula* offers an example of a very suitable expression system. Use of *Pichia pastoris* as an expression system is disclosed in EP-A-0926543 and EP-A-1014176. In one embodiment the micro-organism is free of active post-translational processing mechanism such as in particular hydroxylation of proline and also hydroxylation of lysine. In another embodiment the host system has an endogenic proline hydroxylation activity by which the recombinant gelatin is hydroxylated in a highly effective way. The selection of a suitable host cell from known industrial enzyme producing fungal host cells specifically yeast cells on the basis of the required parameters described herein rendering the host cell suitable for expression of recombinant gelatin-like proteins suitable in compositions according to the invention in combination with knowledge regarding the host cells and the sequence to be expressed will be possible by a person skilled in the art.

Thus, in one aspect the invention a method is provided for producing a non-natural recombinant gelatin according to present invention, said method comprising the steps of preparing an expression vector comprising a nucleic acid sequence encoding a non-natural recombinant gelatin polypeptide as described hereinabove operably linked to a suitable promoter, transforming a yeast species, preferably a methylotrophic yeast, preferably, *Pichia pastoris*, with said expression vector;

culturing said yeast species under suitable fermentation conditions to allow expression of said nucleic acid sequence and secretion of the non-natural gelatin of this invention, and optionally isolating said polypeptide from the culture medium.

The polypeptide can also be recovered from the host cells, but this is not preferred. Preferably said non-natural recombinant gelatin is produced at a level of at least 5 g/l supernatant, preferably at least 7 g/l and more preferably in an amount of more than 9 g/l supernatant. Even secretion levels as high as 12, 13, 15 or 17 or 19 g/l or more have been achieved Preferably the present non-natural recombinant gelatin polypeptide is isolated and purified.

Also mutant host strains may be used, e.g. strains deficient in one or more proteolytic enzymes, although this is not necessary according to the present invention, as the recombinant polypeptides are highly stable and resistant to proteolysis.

SEQUENCES

SEQ ID NO 1: PCM-monomer
SEQ ID NO 2: PCM
SEQ ID NO 3: PCM-dimer
SEQ ID NO 4: PCM2
SEQ ID NO 5: PCM-tetramer
SEQ ID NO 6: PCM4

EXAMPLES

Example 1

Similar to the construction of pPIC9-P4, which has been described in detail in Werten et al. (2001, Protein Engineering 14:447-454; which is incorporated by reference herein) the vector comprising the gene for PCM, has been prepared.

The BglII-Not fragment from pPIC9-PCM containing the AOX1 promoter and the gene for PCM was subcloned from pPIC9-PCM into pPICZ A digested with the same enzymes to yield pPICZ-PCM. The DraIII site in the Zeocin resistance gene from pPICZ-PCM was removed by site-directed mutagenesis to render the DraIII site in the gene for PCM unique. The HindIII-PflMI fragment containing the PCM gene from pPICZ-PCM was subcloned into pPICZ-PCM digested with DraIII and HindIII.

This resulted in the formulation of plasmid pPICZ-PCM2. Plasmid pPICZ-PCM4 was generated by subcloning the HindIII-PflMI fragment from pPICZ-PCM2 into the same plasmid digested with HindIII and DraIII.

The plasmids pPICZ-PCM, pPICZ-PCM2 and pPICZ-PCM4 were linearized with PmeI and transformed into *P. pastoris* X-33. Multicopy integrants were selected on 1.0 and 1.5 mg/ml of Zeocin. Manufacturer's (Invitrogen) protocols were followed.

Representative strains resulting from these transformations were grown in high-density cell cultures under standard fermentation conditions (at a pH of about 4), and the yield of the relevant gelatins in the supernatants was determined using HPLC (using BSA as a standard).

Yields obtained were:
PCM9 g/l
PCM2 12 g/l
PCM4 17 g/l
Amino Acid Sequence of PCM (SEQ ID NO: 2)

GPPGEPGNPGSPGNQGQPGNRGDKGSPGNPGQPGNEGQPGQPGQNGQPGE

PGSNGPQGSQGNPGKNGQPGSPGSRGDQGSPGNQGSPGQPGNPGQPGEQG

KPGNQGPAGEPGNPGSPGNQGQPGNKGSPGNPGQPGNRGDEGQPGQPGQN

GQPGEPGSNGPQGSQGNPGKNGQPGSPGSQGSPGNQGSPGQPGNPGQPGE

RGDQGKPGNQGPAGEPGNPGSPGNQGQPGNKGSPGNPGQPGNEGQPGQPG

QRGDNGQPGEPGSNGPQGSQGNPGKNGQPGSPGSQGSPGNQGSPGQPGNP

GQPGEQGKPGNRGDQGPAGG

Calculated molecular weight is 29.7 kDa; comprising 6 RGD motifs;

A multimer PCM2 comprising the PCM monomer sequence SEQ ID NO 1 comprising 2 repeats was made (SEQ ID NO: 4):

GPPGEPGNPGSPGNQGQPGNRGDKGSPGNPGQPGNEGQPGQPGQNGQPGE

PGSNGPQGSQGNPGKNGQPGSPGSRGDQGSPGNQGSPGQPGNPGQPGEQG

KPGNQGPAGEPGNPGSPGNQGQPGNKGSPGNPGQPGNRGDEGQPGQPGQN

GQPGEPGSNGPQGSQGNPGKNGQPGSPGSQGSPGNQGSPGQPGNPGQPGE

RGDQGKPGNQGPAGEPGNPGSPGNQGQPGNKGSPGNPGQPGNEGQPGQPG

QRGDNGQPGEPGSNGPQGSQGNPGKNGQPGSPGSQGSPGNQGSPGQPGNP

GQPGEQGKPGNRGDQGPAGEPGNPGSPGNQGQPGNRGDKGSPGNPGQPGN

EGQPGQPGQNGQPGEPGSNGPQGSQGNPGKNGQPGSPGSRGDQGSPGNQG

SPGQPGNPGQPGEQGKPGNQGPAGEPGNPGSPGNQGQPGNKGSPGNPGQP

GNRGDEGQPGQPGQNGQPGEPGSNGPQGSQGNPGKNGQPGSPGSQGSPGN

QGSPGQPGNPGQPGERGDQGKPGNQGPAGEPGNPGSPGNQGQPGNKGSPG

NPGQPGNEGQPGQPGQRGDNGQPGEPGSNGPQGSQGNPGKNGQPGSPGSQ

GSPGNQGSPGQPGNPGQPGEQGKPGNRGDQGPAGG

Calculated molecular weight is 59.0 kDa; comprising 12 RGD motifs;

A multimer PCM4 comprising the PCM monomer sequence SEQ ID NO 1 comprising 4 repeats was made (SEQ ID NO: 6):

GPPGEPGNPGSPGNQGQPGNRGDKGSPGNPGQPGNEGQPGQPGQNGQPGE

PGSNGPQGSQGNPGKNGQPGSPGSRGDQGSPGNQGSPGQPGNPGQPGEQG

KPGNQGPAGEPGNPGSPGNQGQPGNKGSPGNPGQPGNRGDEGQPGQPGQN

GQPGEPGSNGPQGSQGNPGKNGQPGSPGSQGSPGNQGSPGQPGNPGQPGE

RGDQGKPGNQGPAGEPGNPGSPGNQGQPGNKGSPGNPGQPGNEGQPGQPG

QRGDNGQPGEPGSNGPQGSQGNPGKNGQPGSPGSQGSPGNQGSPGQPGNP

GQPGEQGKPGNRGDQGPAGEPGNPGSPGNQGQPGNRGDKGSPGNPGQPGN

EGQPGQPGQNGQPGEPGSNGPQGSQGNPGKNGQPGSPGSRGDQGSPGNQG

SPGQPGNPGQPGEQGKPGNQGPAGEPGNPGSPGNQGQPGNKGSPGNPGQP

GNRGDEGQPGQPGQNGQPGEPGSNGPQGSQGNPGKNGQPGSPGSQGSPGN

QGSPGQPGNPGQPGERGDQGKPGNQGPAGEPGNPGSPGNQGQPGNKGSPG

NPGQPGNEGQPGQPGQRGDNGQPGEPGSNGPQGSQGNPGKNGQPGSPGSQ

GSPGNQGSPGQPGNPGQPGEQGKPGNRGDQGPAGEPGNPGSPGNQGQPGN

RGDKGSPGNPGQPGNEGQPGQPGQNGQPGEPGSNGPQGSQGNPGKNGQPG

SGSRGDQGSPGNQGSPGQPGNPGQPGEQGKPGNQGPAGEPGNPGSPGNQG

QPGNKGSPGNPGQPGNRGDEGQPGQPGQNGQPGEPGSNGPQGSQGNPGKN

GQPGSPGSQGSPGNQGSPGQPGNPGQPGERGDQGKPGNQGPAGEPGNPGS

PGNQGQPGNKGSPGNPGQPGNEGQPGQPGQRGDNGQPGEPGSNGPQGSQG

NPGKNGQPGSPGSQGSPGNQGSPGQPGNPGQPGEQGKPGNRGDQGPAGEP

GNPGSPGNQGQPGNRGDKGSPGNPGQPGNEGQPGQPGQNGQPGEPGSNGP

QGSQGNPGKNGQPGSPGSRGDQGSPGNQGSPGQPGNPGQPGEQGKPGNQG

PAGEPGNPGSPGNQGQPGNKGSPGNPGQPGNRGDEGQPGQPGQNGQPGEP

GSNGPQGSQGNPGKNGQPGSPGSQGSPGNQGSPGQPGNPGQPGERGDQGK

PGNQGPAGEPGNPGSPGNQGQPGNKGSPGNPGQPGNEGQPGQPGQRGDNG

QPGEPGSNGPQGSQGNPGKNGQPGSPGSQGSPGNQGSPGQPGNPGQPGEQ

GKPGNRGDQGPAGG

Example 2

Preparation of Microcarriers Beads

Polystyrene beads with an average diameter of 100 micrometers are used. The heterobifunctional cross-linking agent, BBA-EAC-NOS, is used to covalently immobilise gelatin onto polystyrene beads. The BBA-EAC-NOS is added to the polystyrene beads and allowed to adsorb. Next, gelatin is added and is allowed to react with the NOS synthetic polymer to produce covalent coupling to the spacer. Then the beads are photoactivated (at 320 nm) to covalently immobilise the spacer (and covalently coupled gelatin) to the polystyrene beads. Finally, loosely adherent gelatine is removed by overnight washing with the mild detergent Tween 20 in phosphate buffered saline (pH 7.2).

Cell Types and Culture Conditions

Green monkey kidney (Vero) cells, Chinese hamster ovary (CHO) cells, normal rat kidney fibroblast (NRK-49F) cells, and Madin Darby canine kidney (MDCK) cells were purchased from ATCC. All four cell types were passaged and maintained in 75 cm$^2$ flasks at 37 DEG C. in a 5% $CO_2$ environment. Vero and NRK-49F cells were cultured in Dulbecco's Modified Eagles's Medium (DMEM), CHO cells were cultured in Ham's F-12 Nutrient Mixture, and MDCK cells were cultured in Minimum Essential Medium (MEM) with Earle's salts.

With the Vero and CHO cells, the medium was supplemented with 10% fetal bovine serum (FBS), 2 mM L-glutamine, 20 mM HEPES buffer, 1 mM sodium pyruvate, 100 ug/ml streptomycin, and 100 units/ml penicillin (final pH 7.1). With the NRK-49F cells, the DMEM was supplemented with 5% FBS, 2 mM L-glutamine, 1 mM sodium pyruvate, non-essential amino acids (0.1 mM each), 100 μg/ml streptomycin, 100 units/ml penicillin, and 0.25 μg/ml of amphotericin B (final pH 7.1). With the MDCK cells, the MEM was supplemented with 10% FBS, 2 mM L-glutamine, non-essential amino acids (0.1 mM each), and 100 μg/ml streptomycin, 100 units/ml penicillin, and 0.25 μg/ml of amphotericin B (final pH 7.1).

In order to standardise the physiology of cells prior to each experiment, cells were passed into 150 cm$^2$ flasks 2 to 3 days prior to inoculation of microcarrier beads. Cells were trypsinised (0.05% trypsin, 0.53 mM EDTA in PBS) for removal from the flasks. For the microcarrier experiments, the cells were centrifuged to remove the trypsin medium and resuspended to about $1.\text{times}.10^6$ cells/ml in culture medium. The viable cell concentration was determined by Trypan dye exclusion (0.4% Trypan blue in 0.9% saline).

Cell Culture and Assays in Spinner Flasks

For the cell attachment assay, 20 mg/ml of coated polystyrene beads were used and the cell concentration was $1.5.\text{times}.10^5$ cells/ml for each cell type.

Microcarriers were cultured with 100 ml cultures being maintained in 250 ml spinner vessels and stirred with suspended magnetic impellers (50 rpm).

The kinetics of cell attachment were assayed as a decrease in supernatant cell concentration. For sample removal the agitation was stopped briefly (about 30 seconds) at which time the microcarriers settled and a supernatant sample was removed for cell quantitation as described below.

For the cell counts, the cells were stained by mixing with an equal volume of crystal violet (0.1% w/w) in 0.1 M citric acid, and then counted with a hemocytometer. Cell depletion from the medium was used as an indicator of cells attached to heads.

To verify that cells removed from the medium were indeed attached to microcarriers (and not lysed), cells attached to microcarriers were quantitated at the end of each cell attachment assay. One ml aliquots of well-agitated carrier medium were removed, the microcarriers were allowed to settle, and the settled microcarriers were resuspended in crystal violet/citric acid as described above. After incubating 1 hour at 37° C., the suspension was sheared by sucking into and out of a Pasteur pipette to release nuclei, which were quantitated with a haemocytometer.

Gelatin PCM (SEQ ID NO: 2) was used as a microcarrier coating according to the foregoing procedure and compared with a reference RGD-enriched gelatin with sequence identifier number 2 having four RGD sequences as disclosed in US 2006/0241032. PCM gave improved results in terms of numbers of cell depletion from the starting culture medium and also in terms of cell attachment to microcarriers. This improvement may be due to improved stability of the PCM gelatine compared to the sequence with identifier number 2 as disclosed in US 2006/0241032.

Also PCM2 and PCM4 are used as a microcarrier coating according to the foregoing procedure and compared with a trimer, a tetramer and a quintamer of RGD-enriched gelatin with sequence identifier number 2 as disclosed in US 2006/0241032. Probably due to their improved stability, PCM2 and PCM4 show improved cell attachment to microcarriers compared to the multimeric gelatins based on the sequence with identifier number 2 as disclosed in US 2006/0241032. Also particle size measurements of PCM2 and PCM4 coated microcarriers after keeping the coated microcarriers for 24 hours and immediately after the cell attachment assay show a more homogeneous distribution of particle sizes compared to the multimeric gelatins based on the sequence with identifier number 2 as disclosed in US 2006/0241032.

The invention claimed is:

1. A non-natural recombinantly produced gelatin polypeptide comprising or consisting of an amino acid sequence with at least 90% sequence identity to SEQ ID NO: 1 and at least one RGD motif.

2. The non-natural recombinantly produced gelatin polypeptide according to claim 1, wherein the polypeptide comprises or consists of an amino acid sequence with at least 95% sequence identity to SEQ ID NO: 1.

3. The non-natural recombinantly produced gelatin polypeptide according to claim 1, wherein the polypeptide comprises or consists of the amino acid sequence of SEQ ID NO: 1.

4. The non-natural recombinantly produced gelatin polypeptide according to claim 1, wherein the polypeptide consists of the amino acid sequence of SEQ ID NO: 1.

5. A controlled release, hemostat, dermal filler or pharmaceutical composition comprising the non-natural recombinantly produced gelatin polypeptide according to claim 1.

6. A non-natural recombinantly produced gelatin polypeptide which is a polymeric recombinant gelatin comprising or consisting of at least two repeats of the recombinant gelatin polypeptide according to claim 1.

7. The non-natural recombinantly produced gelatin polypeptide according to claim 6, wherein said repeats are identical in amino acid sequence.

8. The non-natural recombinantly produced gelatin polypeptide according to claim 7, wherein the repeats contain less than 7 intervening amino acids between the monomeric repeat units.

9. A cell support comprising the non-natural recombinantly produced gelatin polypeptide according to claim 1.

10. The cell support according to claim 9, said cell support being selected from the group consisting of a recombinant gelatin coated implant or transplant material, a recombinant gelatin coated scaffold for tissue engineering, a dental product, a wound healing product, an artificial skin matrix material and a tissue adhesive.

11. A method for producing a non-natural recombinantly produced gelatin polypeptide according to claim 1, said method comprising:
 (a) preparing an expression vector comprising a nucleic acid sequence encoding the non-natural recombinantly produced gelatin polypeptide according to claim 1 operably linked to a suitable promoter;
 (b) transforming a yeast species with said expression vector;
 (c) culturing said yeast species under suitable fermentation conditions to allow expression of said nucleic acid sequence; and
 (d) optionally isolating said polypeptide from the culture medium and/or the host cells.

12. A method for inhibition of cancer metastasis, for prevention of platelet aggregation or for preventing after surgery tissue adhesion comprising contacting a surgical site with the non-natural recombinantly produced gelatin polypeptide according to claim 1.

* * * * *